(12) United States Patent
Lynch et al.

(10) Patent No.: US 6,242,216 B1
(45) Date of Patent: Jun. 5, 2001

(54) NUCLEIC ACIDS ENCODING A FUNCTIONAL HUMAN PURINORECEPTOR P2X2 AND P2X4, AND METHODS OF PRODUCTION AND USE THEREOF

(75) Inventors: Kevin J. Lynch, Gurnee; Edward C. Burgard, Libertyville; Randy E. Metzger, Gurnee; Wende Niforatos, Chicago; Edward B. Touma, Chicago; Tim Van Biesen, Chicago, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/191,608

(22) Filed: Nov. 13, 1998

Related U.S. Application Data

(63) Continuation-in-part of application No. 09/137,458, filed on Aug. 20, 1998.
(60) Provisional application No. 60/065,822, filed on Nov. 14, 1997.

(51) Int. Cl.⁷ .............................. C12N 15/12; C12N 5/10
(52) U.S. Cl. .................. 435/69.1; 435/252.3; 435/320.1; 536/23.5
(58) Field of Search .............................. 435/69.1, 252.3, 435/320.1; 536/23.5

(56) References Cited

U.S. PATENT DOCUMENTS

| | | |
|---|---|---|
| 5,607,836 | 3/1997 | Boucher et al. . |
| 5,733,916 | 3/1998 | Neely . |

FOREIGN PATENT DOCUMENTS

| | | |
|---|---|---|
| 9533048 | 7/1995 | (WO) . |
| 9533048 | 12/1995 | (WO) . |
| 9741222 | 6/1997 | (WO) . |
| 9818916 | 7/1998 | (WO) . |
| 9842835 | 10/1998 | (WO) . |

OTHER PUBLICATIONS

Brändle, U., et al., "Desensitization of the P2X$_2$ receptor controlled by alternative splicing", *FEBS Letters*, 404:294–298 (1997).

Cook, S. P., et al., "Distinct ATP receptors on pain–sensing and stretch–sensing neurons", *letters to nature*, 387:505–508 (1997).

Garcia–Guzman, M., et al., "Molecular characterization and pharmacological properties of the human P2X$_3$ purinoceptor", *Molecular Brain Research*, 47:59–66 (1997).

Garcia–Guzman, M., et al., "Characterization of Recombinant Human P2X4 Receptor Reveals Pharmacological Differences to the Rat Homologue", *The American Soc of Pharm. And Exp. Therapeutics*, 51:109–118 (1997).

Koshimizu, T–a., et al., "Functional Role of Alternative Splicing in Pituitary P2X$_2$ Receptor–Channel Activation and Desensitization", *Molecular Endocrinology*, 12(7):901–913 (19998).

Urano, T., et al., "Cloning of P2XM, a Novel Human P2X Receptor Gene Regulated by p53", *Cancer Research*, 57:3281–3287 (1997).

McMahon R. A.: "H. sapiens P2X2A receptor" Accession No. AF109387, XP002130973, Jul. 7, 1999.

Brake A. J. et al.: "New structural motif for ligand–gated ion channels defined by an ionotropic ATP receptor" Nature, vol. 371, pp. 519–523, XP002130970, Oct. 6, 1994.

Le K. T. et al.: "Primary structure and expression of a naturally truncated human P2X ATP receptor subunit from brain and immune system" FEBS Letters, vol. 418, 1997, pp. 195–199, XP002131048.

Simon J. et al.: "Localization and functional expression of splice variants of the P2X2 receptor" Mol. Pharm., vol. 52, 1997, pp. 237–248, XP000876936.

Housley G. D. et al.: "Identification of a short form of the P2X1R1–purinoreceptor subunit produced by alternative splicing in the pituitary and cochlea" Biochem. Biophys. Res. Com., vol. 212, No. 2, Jul. 17, 1995, pp. 501–508, XP002130971.

King B. & Burnstock G.: "P2–receptor nomenclature" Nov. 29, 1996—XP002130972–.

Michel A. D. et al.: "A comparison of the binding characteristics of recombinant P2X1 and P2X2 purinoceptors" British Journal of Pharmacology, GB, Basingstoke, Hants, vol. 118, No. 7, Jan. 1, 1996—pp. 1806–1812 XP000616428.

Lewis C. et al.: "Coexpression of P2X2 and P2X3 receptor subunits can account for ATP–gated currents in sensory neurons" Nature, GB, Macmillan Journals LTD. London, vol. 377, No. 377, Oct. 5, 1995, pp. 432–435, XP002098923.

Bhagwat SS Williams M.: "P2 purine and pyrimidine receptors: emerging superfamilies of G–protein–coupled and ligand–gated ion channel receptors" European Journal of Medicinal Chemistry . Chimica Therapeutica, FR, Editions Scientifique Elsevier, Paris, vol. 32, No. 3, Jan. 1, 1997, pp. 183–193, XP004075420.

*Primary Examiner*—John Ulm
(74) *Attorney, Agent, or Firm*—Cheryl L. Becker; Mimi C. Goller

(57) ABSTRACT

Human P2X$_2$ and P2X$_4$ purinergic receptor polypeptides are provided. Nucleic acid molecules encoding the aforementioned human P2X receptor polypeptide, and vectors and host cells containing such nucleic acid molecules, are also provided. In addition, methods are provided for producing these P2X receptor polypeptide, as are methods of using such polypeptides and host cells that express the same to screen for compounds having activity on P2X$_2$ and P2X$_4$ receptors. Further, therapeutic uses involving aspects of these receptors are contemplated.

20 Claims, 15 Drawing Sheets

CTCATCAAGGCCTACGGGATCCGCATTGACGTCATTGTGCATGGACAGGCCGGG
AAGTTCAGCCTGATTCCCACCATTATTAATCTGGCCACAGCTCTGACTTCCGTCG
GGGTGGGCTCCTTCCTGTGCGACTGGATCTTGCTAACATTCATGAACAAAAACAA
GGTCTACAGCCATAAGAAATTTGACAAGGTGTGTACGCCGAGCCACCCCTCAGG
TAG

FIG.1

GCTCATCAAGGCCTACGGGATCCGCATTGACGTCATTGTGCATGGACAGGCCGG
GAAGTTCAGCCTGATTCCCACCATTATTAATCTGGCCACAGCTCTGACTTCCGTC
GGGGTGGGCTCCTTCCTGTGCGACTGGATCTTGCTAACATTCATGAACAAAAACA
AGGTCTACAGCCATAAGAAATTTGACAAGGTGTGTACGCCGAGCCACCCCTCAG
GTAGCTGGCCTGTGACCCTTGCCCGTGTATTGGGCCAGGCCCCTCCCGAACCC
GGCCACCGCTCCGAGGACCAGCACCCCAGCCCTCCATCAGGCCAGGAGGGCCA
ACAAGGGGCAGAGTGTGGCCCAGCCTTCCCGCCCCTGCGGCCTTGCCCCATCT
CTGCCCCTTCTGAGCAGATGGTGGACACTCCTGCCTCCGAGCCTGCCCAAGCCT
CCACACCCACAGACCCCAAAGGTTTGGCTCAACTCTGAGCTCCTTTCCATCTCAC
TGGACTGCAGACCCGGCCTGGTGGGCCAGAGAGTCCCCAGCTAGGGACCTGC
ACGTGGACGTGGGCACCTCAGTAGCGGAGCATCTCCACGAAACGGGGCACCAC
AGGATCCCTGTGCAAGGGCTGGGGGCACGCTCTGGCCCCAGGCTTGTGCCCCA
CCCTGGCATACAGCCCCTGACACCTCCTCCCCAGCTGGTCCCTACAGGGCTGCT
CACTTCCCATCACCTCTCACAGCCACCTGGAACCCAAGCCAGCTGAGCTCTGAG
GGGCTCTGCTCCCGGTCTTGGGCCCTGGGAACCCCACCCCACCCCACCCCACA
GGCGTTGTAACCTCGAATCTGCCCAGACTCTTCCCTTAGAAGTCACAACATACTC
AGTCCAATAAACCTGTGAGCAGAAAAAAAAAAAAAAAAAAGGGCGGCCGC

FIG.2

GSP 1    ATGAATGTTAGCAAGATCCA

FIG. 3A

GSP 2    CAUCAUCAUCAUCACCCCGACGGAAGTCAGAG

FIG. 3B

GSP3    CCTGTCCATGCACAATGACG

FIG. 3C

Anchor Primer

CUACUACUACUAGGCCACGCGTCGACTAGTACGGGNNGGGNNGGGNNG

FIG. 3D

Universal Amplification Primer

CUACUACUACUAGGCCACGCGTCGACTAGTAC

FIG. 3E

GAATTCGGCTTCTACTACTACTAGGCCACGCGTCGACTAGTACGGGGGGGGGG
GGGGGGGCCCCGGTGGAAGATGGGGCCTCTGTCAGCCAATTTCTGGGTACGAT
GGCCCCAAATTTCGCGATCCTCATCAAGAACAGCATCCATTACCCCAAATTCCAC
TTCTCCAAGGGCAACATCGCCGACCGCACAGACGGGTACCTGAAGCGCTGCAC
GTTCCACGAGGCCTCCGACCTTTACTGCCCCATCTTCAAGCTGGGCTTTATCGTG
GAGAAGGCTGGGGAGAGCTTCACAGAGCTCGCACACAAGGGTGGTGTCATCGG
GGTCATTATCAACTGGGACTGTGACCTGGACCTGCCTGCATCGGAGTGCAACCC
CAAGTACTCCTTCCGGAGGCTTGACCCCAAGCACGTGCCTGCCTCGTCAGGCTA
CAACTTCAGGTTTGCCAAATACTACAAGATCAATGGCACCACCACCCGCAGCTCA
TCAAGGCCTACGGGATCCGCATTGACGTCATTGTGCATGGACAGG

FIG.4

X2-539F     TCCTTCCTGTGCGACTGGATCTTG

FIG.5A

X2-869R     CAAACCTTTGGGGTCTGTGGGTG

FIG.5B hP2X25'     CCACCATGGCCGCCGCCCAGCCCAAGTA

FIG.6A hP2X23'     GGAAAGGAGCTCAGAGTTGAGCCAAACC

FIG.6B hP2x2a

CCACCATGGCCGCCGCCCAGCCCAAGTACCCCGCCGGGGCGACCGCCCGGCG
CCTGGCCCGGGGCTGCTGGTCCGCCCTCTGGGACTACGAGACGCCCAAGGTGA
TCGTGGTGAGGAACCGGCGCCTGGGGGTCCTGTACCGCGCCGTGCAGCTGCTC
ATCCTGCTCTACTTCGTGTGGTACGTATTCATCGTGCAGAAAAGCTACCAGGAGA
GCGAGACGGGCCCCGAGAGCTCCATCATCACCAAGGTCAAGGGGATCACCACG
TCCGAGCACAAAGTGTGGGACGTGGAGGAGTACGTGAAGCCCCCCGAGGGGG
GCAGCGTGTTCAGCATCATCACCAGGGTCGAGGCCACCCACTCCCAGACCCAG
GGAACCTGCCCCGAGAGCATAAGGGTCCACAACGCCACCTGCCTCTCCGACGC
CGACTGCGTGGCTGGGGAGCTGGACATGCTGGGAAACGGCCTGAGGACCGGG
CGCTGTGTGCCCTATTACCAGGGGCCCTCCAAGACCTGCGAGGTGTTCGGCTG
GTGCCCGGTGGAAGATGGGGCCTCTGTCAGCCAATTTCTGGGTACGATGGCCC
CAAATTTCACCATCCTCATCAAGAACAGCATCCACTACCCCAAATTCCACTTCTCC
AAGGGCAACATCGCCGACCGCACAGACGGGTACCTGAAGCGCTGCACGTTCCA
CGAGGCCTCCGACCTCTACTGCCCCATCTTCAAGCTGGGCTTTATCGTGGAGAA
GGCTGGGGAGAGCTTCACAGAGCTCGCACACAAGGGTGGTGTCATCGGGGTCA
TTATCAACTGGGACTGTGACCTGGACCTGCCTGCATCGGAGTGCAACCCCAAGT
ACTCCTTCCGGAGGCTTGACCCCAAGCACGTGCCTGCCTCGTCAGGCTACAACT
TCAGGTTTGCCAAATACTACAAGATCAATGGCACCACCACCCGCACGCTCATCAA
GGCCTACGGGATCCGCATTGACGTCATTGTGCATGGACAGGCCGGGAAGTTCA
GCCTGATTCCCACCATTATTAATCTGGCCACAGCTCTGACTTCCGTCGGGGTGG
GCTCCTTCCTGTGCGACTGGATCTTGCTAACATTCATGAACAAAAACAAGGTCTA
CAGCCATAAGAAATTTGACAAGGTGTGTACGCCGAGCCACCCCTCAGGTAGCTG
GCCTGTGACCCTTGCCCGTGTATTGGGCCAGGCCCCTCCCGAACCCGGCCACC
GCTCCGAGGACCAGCACCCCAGCCCTCCATCAGGCCAGGAGGGCCAACAAGGG
GCAGAGTGTGGCCCAGCCTTCCCCCCCTGCGGCCTTGCCCCATCTCTGCCCCT
TCTGAGCAGATGGTGGACACTCCTGCCTCCGAGCCTGCCCAAGCCTCCACACCC
ACAGACCCCAAAGGTTTGGCTCAACTCTGAGCTCCTTTCCGGGCT

FIG. 7A hP2X2b

CCACCATGGCCGCCGCCCAGCCCAAGTACCCCGCCGGGGCGACCGCCCGGCG
CCTGGCCCGGGGCTGCTGGTCCGCCCTCTGGGACTACGAGACGCCCAAGGTGA
TCGTGGTGAGGAACCGGCGCCTGGGGGTCCTGTACCGCGCCGTGCAGCTGCTC
ATCCTGCTCTACTTCGTGTGGTACGTATTCATCGTGCARAAAAGCTACCAGGAGA
GCGAGACGGGCCCCGAGAGCTCCATCATCACCAAGGTCAAGGGGATCACCACG
TCCGAGCACAAAGTGTGGGACGTGGAGGAGTACGTGAAGCCCCCCGAGGGGG
GCAGCGTGTTCAGCATCATCACCAGGGTCGAGGCCACCCACTCCCAGACCCAG
GGAACCTGCCCCGAGAGCATAAGGGTCCACAACGCCACCTGCCTCTCCGACGC
CGACTGCGTGGCTGGGGAGCTGGACATGCTGGGAAACGGCCTGAGGACCGGG
CGCTGTGTGCCCTATTACCAGGGGCCCTCCAAGACCTGCGAGGTGTTCGGCTG
GTGCCCGGTGGAAGATGGGGCCTCTGTCAGCCAATTTCTGGGTACGATGGCCC
CAAATTTCACCATCCTCATCAAGAACAGCATCCACTACCCCAAATTCCACTTCTCC
AAGGGCAACATCGCCGACCGCACAGACGGGTACCTGAAGCGCTGCACGTTCCA
CGAGGCCTCCGACCTCTACTGCCCCATCTTCAAGCTGGGCTTTATCGTGGAGAA
GGCTGGGGAGAGCTTCACAGAGCTCGCACACAAGGGTGGTGTCATCGGGGTCA
TTATCAACTGGGACTGTGACCTGGACCTGCCTGCATCGGAGTGCAACCCCAAGT
ACTCCTTCCGGAGGCTTGACCCCAAGCACGTGCCTGCCTCGTCAGGCTACAACT
TCAGGTTTGCCAAATACTACAAGATCAATGGCACCACCACCCGCACGCTCATCAA
GGCCTACGGGATCCGCATTGACGTCATTGTGCATGGACAGGCCGGGAAGTTCA
GCCTGATTCCCACCATTATTAATCTGGCCACAGCTCTGACTTCCGTCGGGGTGG
GCTCCTTCCTGTGCGACTGGATCTTGCTAACATTCATGAACAAAAACAAGGTCTA
CAGCCATAAGAAATTTGACAAGGTGTGTACGCCGAGCCACCCCTCAGGTAGCTG
GCCTGTGACCCTTGCCCGTGTATTGGGCCAGGCCCCTCCCGAACCCGGCCACC
GCTCCGAGGACCAGCACCCCAGCCCTCCATCAGGCCAGGAGGGCCAACAAGGG
GCAGAGTGTGGCCCAGCCTTCCCGCCCCTGCGGCCTTGCCCCATCTCTGCCCCT
TCTGAGCAGATGGTGGACACTCCTGCCTCCGAGCCTGCCCAAGCCTCCACACCCACAGA
CCCCAAAGGTTTGGCTCAACTTTGA

FIG. 7B hP2X2c

CCACCATGGCCGCCGCCCAGCCCAAGTACCCCGCCGGGGCGACCGCCCGGCG
CCTGGCCCGGGGCTGCTGGTCCGCCCTCTGGGACTACGAGACGCCCAAGGTGA
TCGTGGTGAGGAACCGGCGCCTGGGGGTCCTGTACCGCGCCGTGCAGCTGCTC
ATCCTGCTCTACTTCGTGTGGTACGTATTCATCGTGCAGAAAAGCTACCAGGAGA
GCGAGACGGGCCCCGAGAGCTCCATCATCACCAAGGTCAAGGGGATCACCACG
TCCGAGCACAAAGTGTGGGACGTGGAGGAGTACGTGAAGCCCCCCGAGAGCAT
AAGGGTCCACAACGCCACCTGCCTCTCCGACGCCGACTGCGTGGCTGGGGAGC
TGGACATGCTGGGAAACGGCCTGAGGACTGGGCGCTGTGCCCTATTACCAG
GGGCCCTCCAAGACCTGCGAGGTGTTCGGCTGGTGCCCGGTGGAAGATGGGGC
CTCTGTCAGCCAATTTCTGGGTACGATGGCCCCAAATTTCACCATCCTCATCAAG
AACAGCATCCACTACCCCAAATTCCACTTCTCCAAGGGCAACATCGCCGACCGC
ACAGACGGGTACCTGAAGCGCTGCACGTTCCACGAGGCCTCCGACCTCTACTGC
CCCATCTTCAAGCTGGGCTTTATCGTGGAGAAGGCTGGGGAGAGCTTCACAGAG
CTCGCACACAAGGGTGGTGTCATCGGGGTCATTATCAACTGGGACTGTGACCTGGACCT
GCCTGCATCGGAGTGCAACCCCAAGTACTCCTTCCGGAGGCTTGACCCC
AAGCACGTGCCTGCCTCGTCAGGCTACAACTTCAGGTTTGCCAAATACTACAAGA
TCAATGGCACCACCACCCGCACGCTCATCAAGGCCTACGGGATCCGCATTGACG
TCATTGTGCATGGACAGGCCGGGAAGTTCAGCCTGATTCCCACCATTATTAATCT
GGCCACAGCTCTGACTTCCGTCGGGGTGGGCTCCTTCCTGTGCGACTGGATCTT
GCTAACATTCATGAACAAAAACAAGGTCTACAGCCATAAGAAATTTGACAAGGTG
TGTACGCCGAGCCACCCCTCAGGTAGCTGGCCTGTGACCCTTGCCCGTGTATTG
GGCCAGGCCCCTCCCGAACCCGGCCACCGCTCCGAGGACCAGCACCCCAGCC
CTCCATCAGGCCAGGAGGGCCAACAAGGGGCAGAGTGTGGCCCAGCCTTCCCG
CCCCTGCGGCCTTGCCCCATCTCTGCCCCTTCTGAGCAGATGGTGGACACTCCT
GCCTCCGAGCCTGCCCAAGCCTCCACACCCACAGACCCCAAAGGTTTGGCTCAA
CTCTGA

FIG. 7C hP2X2d

CCACCATGGCCGCCGCCCAGCCCAAGTACCCCGCCGGGGCGACCGCCCGGCG
CCTGGCCCGGGGCTGCTGGTCCGCCCTCTGGGACTACGAGACGCCCAAGGTGA
TCGTGGTGAGGAACCGGCGCCTGGGGGTCCTGTACCGCGCCGTGCAGCTGCTC
ATCCTGCTCTACTTCGTGTGGTACGTATTCATCGTGCARAAAAGCTACCAGGAGA
GCGAGACGGGCCCCGAGAGCTCCATCATCACCAAGGTCAAGGGGATCACCACG
TCCGAGCACAAAGTGTGGGACGTGGAGGAGTACGTGAAGCCCCCCGAGGGGG
GCAGCGTGTTCAGCATCATCACCAGGGTCGAGGCCACCCACTCCCAGACCCAG
GGAACCTGCCCCGAGAGCATAAGGGTCCACAACGCCACCTGCCTCTCCGACGC
CGACTGCGTGGCTGGGGAGCTGGACATGCTGGGAAACGGCCTGAGGACCGGG
CGCTGTGTGCCCTATTACCAGGGGCCCTCCAAGACCTGCGAGGTGTTCGGCTG
GTGCCCGGTGGAAGATGGGGCCTCTGTCAGCCAATTTCTGGGTACGATGGCCC
CAAATTTCACCATCCTCATCAAGAACAGCATCCACTACCCCAAATTCCACTTCTCC
AAGGGCAACATCGCCGACCGCACAGACGGGTACCTGAAGCGCTGCACGTTCCA
CGAGGCCTCCGACCTCTACTGCCCCATCTTCAAGCTGGGCTTTATCGTGGAGAAGGCTG
GGGAGAGCTTCACAGAGCTCGCACACAAGGGTGGTGTCATCGGGGTCA
TTATCAACTGGGACTGTGACCTGGACCTGCCTGCATCGGAGTGCAACCCCAAGT
ACTCCTTCCGGAGGCTTGACCCCAAGCACGTGCCTGCCTCGTCAGGCTACAACT
TCAGGTTTGCCAAATACTACAAGATCAATGGCACCACCACCCGCACGCTCATCAA
GGCCTACGGGATCCGCATTGACGTCATTGTGCATGGACAGGCCGGGAAGTTCA
GCCTGATTCCCACCATTATTAATCTGGCCACAGCTCTGACTTCCGTCGGGGTGGT
AAGGAACCCTCTCTGGGGTCCCAGCGGGTGCGGGGGGTCCACCAGGCCCTTAC
ACACCGGTCTCTGCTGGCCCCAGGGCTCCTTCCTGTGCGACTGGATCTTGCTAA
CATTCATGAACAAAAACAAGGTCTACAGCCATAAGAAATTTGACAAGGTGTGTAC
GCCGAGCCACCCCTCAGGTAGCTGGCCTGTGACCCTTGCCCGTGTATTGGGCC
AGGCCCCTCCCGAACCCGGCCACCGCTCCGAGGACCAGCACCCCAGCCCTCCA
TCAGGCCAGGAGGGCCAACAAGGGGCAGAGTGTGGCCCAGCCTTCCCGCCCCT
GCGGCCTTGCCCCATCTCTGCCCCTTCTGAGCAGATGGTGGACACTCCTGCCTC
CGAGCCTGCCCAAGCCTCCACACCCACAGACCCCAAAGGTTTGGCTCAACTCTG
A

FIG. 7D hP2X2 polypeptide

MAAAQPKYPAGATARRLARGCWSALWDYETPKVIVVRNRRLGVLYRAVQLLILLYFV
WYVFIVQKSYQESETGPESSIITKVKGITTSEHKVWDVEEYVKPPEGGSVFSIITRVEA
THSQTQGTCPESIRVHNATCLSDADCVAGELDMLGNGLRTGRCVPYYQGPSKTCEV
FGWCPVEDGASVSQFLGTMAPNFTILIKNSIHYPKFHFSKGNIADRTDGYLKRCTFHE
ASDLYCPIFKLGFIVEKAGESFTELAHKGGVIGVIINWDCDLDLPASECNPKYSFRRLD
PKHVPASSGYNFRFAKYYKINGTTTRTLIKAYGIRIDVIVHGQAGKFSLIPTIINLATALT
SVGVGSFLCDWILLTFMNKNKVYSHKKFDKVCTPSHPSGSWPVTLARVLGQAPPEP
GHRSEDQHPSPPSGQEGQQGAECGPAFPPLRPCPISAPSEQMVDTPASEPAQAST
PTDPKGLAQL

FIG. 8A hP2X2b

MAAAQPKYPAGATARRLARGCWSALWDYETPKVIVVRNRRLGVLYRAVQLLILLYFV
WYVFIVQKSYQESETGPESSIITKVKGITTSEHKVWDVEEYVKPPEGGSVFSIITRVEA
THSQTQGTCPESIRVHNATCLSDADCVAGELDMLGNGLRTGRCVPYYQGPSKTCEV
FGWCPVEDGASVSQFLGTMAPNFTILIKNSIHYPKFHFSKGNIADRTDGYLKRCTFHE
ASDLYCPIFKLGFIVEKAGESFTELAHKGGVIGVIINWDCDLDLPASECNPKYSFRRLD
PKHVPASSGYNFRFAKYYKINGTTTRTLIKAYGIRIDVIVHGQAGKFSLIPTIINLATALT
SVGVGSFLCDWILLTFMNKNKVYSHKKFDKMVDTPASEPAQASTPTDPKGLAQL

FIG. 8B hP2X2c

MAAAQPKYPAGATARRLARGCWSALWDYETPKVIVVRNRRLGVLYRAVQLLILLYFV
WYVFIVQKSYQESETGPESSIITKVKGITTSEHKVWDVEEYVKPPESIRVHNATCLSD
ADCVAGELDMLGNGLRTGRCVPYYQGPSKTCEVFGWCPVEDGASVSQFLGTMAP
NFTILIKNSIHYPKFHFSKGNIADRTDGYLKRCTFHEASDLYCPIFKLGFIVEKAGESFT
ELAHKGGVIGVIINWDCDLDLPASECNPKYSFRRLDPKHVPASSGYNFRFAKYYKING
TTTRTLIKAYGIRIDVIVHGQAGKFSLIPTIINLATALTSVGVGSFLCDWILLTFMNKNKV
YSHKKFDKVCTPSHPSGSWPVTLARVLGQAPPEPGHRSEDQHPSPPSGQEGQQG
AECGPAFPPLRPCPISAPSEQMVDTPASEPAQASTPTDPKGLAQL

FIG. 8C hP2X2d

MAAAQPKYPAGATARRLARGCWSALWDYETPKVIVVRNRRLGVLYRAVQLLILLYFV
WYVFIVQKSYQESETGPESSIITKVKGITTSEHKVWDVEEYVKPPEGGSVFSIITRVEA
THSQTQGTCPESIRVHNATCLSDADCVAGELDMLGNGLRTGRCVPYYQGPSKTCEV
FGWCPVEDGASVSQFLGTMAPNFTILIKNSIHYPKFHFSKGNIADRTDGYLKRCTFHE
ASDLYCPIFKLGFIVEKAGESFTELAHKGGVIGVIINWDCDLDLPASECNPKYSFRRLD
PKHVPASSGYNFRFAKYYKINGTTTRTLIKAYGIRIDVIVHGQAGKFSLIPTIINLATALT
SVGVVRNPLWGPSGCGGSTRPLHTGLCWPQGSFLCDWILLTFMNKNKVYSHKKFD
KVCTPSHPSGSWPVTLARVLGQAPPEPGHRSEDQHPSPPSGQEGQQGAECGPAF
PPLRPCPISAPSEQMVDTPASEPAQASTPTDPKGLAQL

FIG. 8D

```
hP2X2a pro   MAAAQPKYPAGATARRLARGCWSALWDYETPKVIVVRNRRLGVLYRAVQL   50
hP2X2b pro   MAAAQPKYPAGATARRLARGCWSALWDYETPKVIVVRNRRLGVLYRAVQL
hP2X2c pro   MAAAQPKYPAGATARRLARGCWSALWDYETPKVIVVRNRRLGVLYRAVQL
hP2X2d pro   MAAAQPKYPAGATARRLARGCWSALWDYETPKVIVVRNRRLGVLYRAVQL hP2X2a pro   LILLYFVWYVFIVQKSYQESETGPESSIIITKVKGITTSEHKVWDVEEYVK   100
hP2X2b pro   LILLYFVWYVFIVQKSYQESETGPESSIIITKVKGITTSEHKVWDVEEYVK
hP2X2c pro   LILLYFVWYVFIVQKSYQESETGPESSIIITKVKGITTSEHKVWDVEEYVK
hP2X2d pro   LILLYFVWYVFIVQKSYQESETGPESSIIITKVKGITTSEHKVWDVEEYVK hP2X2a pro   PPEGGSVFSIIITRVEATHSQTQGTCPESIRVHNATCLSDADCVAGELDML   150
hP2X2b pro   PPEGGSVFSIIITRVEATHSQTQGTCPESIRVHNATCLSDADCVAGELDML
hP2X2c pro   PPE··········································
hP2X2d pro   PPEGGSVFSIIITRVEATHSQTQGTCPESIRVHNATCLSDADCVAGELDML hP2X2a pro   GNGLRTGRCVPYYYQGPSKTCEVFGWCPVEDGASVSQFLGTMAPNFTILIK   200
hP2X2b pro   GNGLRTGRCVPYYYQGPSKTCEVFGWCPVEDGASVSQFLGTMAPNFTILIK
hP2X2c pro   ··········································
hP2X2d pro   GNGLRTGRCVPYYYQGPSKTCEVFGWCPVEDGASVSQFLGTMAPNFTILIK hP2X2a pro   NSIHYPKFHFSKGNIADRTDGYLKRCTFHEASDLYCPIFKLGFIVEKAGE   250
hP2X2b pro   NSIHYPKFHFSKGNIADRTDGYLKRCTFHEASDLYCPIFKLGFIVEKAGE
hP2X2c pro   NSIHYPKFHFSKGNIADRTDGYLKRCTFHEASDLYCPIFKLGFIVEKAGE
hP2X2d pro   NSIHYPKFHFSKGNIADRTDGYLKRCTFHEASDLYCPIFKLGFIVEKAGE
```

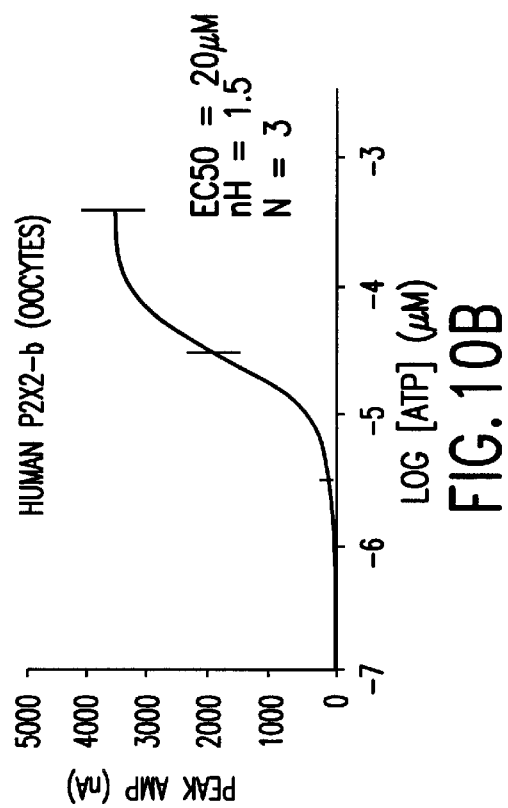
FIG. 10B
FIG. 10D
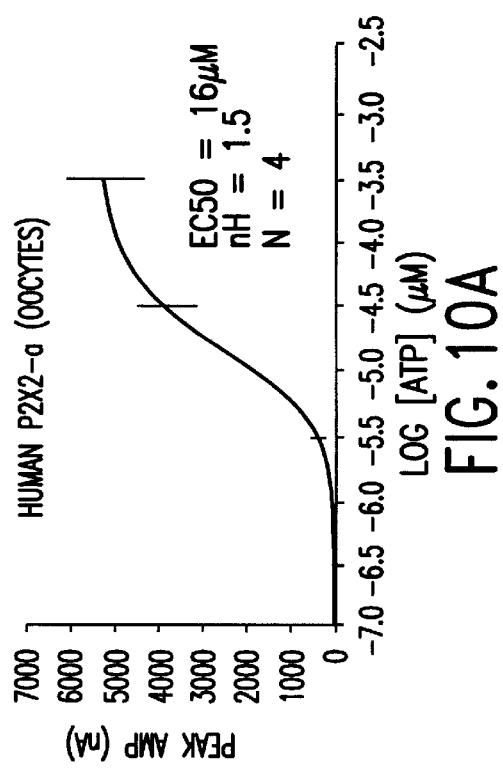
FIG. 10A
FIG. 10C

GAATTCGGCTTTGCGCCACCATGGCGGGCTGCTGCGCCGCGCTGGCGGCCTTC
CTGTTCGAGTACGACACGCCGCGCATCGTGCTCATCCGCAGCCGCAAAGTGGG
GCTCATGAACCGCGCCGTGCAACTGCTCATCCTGGCCTACGTCATCGGGTGGG
TGTTTGTGTGGGAAAAGGGCTACCAGGAAACTGACTCCGTGGTCAGCTCCGTT
ACGACCAAGGTCAAGGGCGTGGCTGTGACCAACACTTCTAAACTTGGATTFCCG
GATCTGGGATGTGGCGGATTATGTGATACCAGCTCAGGAGGAAAACTCCCTCT
TCGTCATGACCAACGTGATCCTCACCATGAACCAGACACAGGGCCTGTGCCCC
GAGATTCCAGATGCGACCACTGTGTGTAAATCAGATGCCAGCTGTACTGCCGG
CTCTGCCGGCACCCACAGCAACGGAGTCTCAACAGGCAGGTGCGTAGCTTTCA
ACGGGTCCGTCAAGACGTGTGAGGTGGCGGCCTGGTGCCCGGTGGAGGATGA
CACACACGTGCCACAACCTGCTTTTTTAAAGGCTGCAGAAAACTTCACTCTTTTG
GTTAAGAACAACATCTGGTATCCCAAATTTAATTTCAGCAAGAGGAATATCCTTC
CCAACATCACCACTACTTACCTCAAGTCGTGCATTATGATGCTAAAACAGATCC
CTTCTGCCCCATATTCCGTCTTGGCAAAATAGTGGAGAACGCAGGACACGGTTT
CCAGGACATGGCCGTGGAGGGAGGCATCATGGGCATCCAGGTCAACTGGGAC
TGCAACCTGGACAGAGCCGCCTCCCTCTGCTTGCCCAGGTACTCCTTCCGCCG
CCTCGATACACGGGACGTTGAGCACAACGTATCTCCTGGCTACAATTTCAGGTT
TGCCAAGTACTACAGAGACCTGGCTGGCAACGAGCAGCGCACGCTCATCAAGG
CCTATGGGCATCCGCTTCGACATCATTGTGTTTGGGAAGGCAGGGAAATTTGACA
TCATCCCCACTATGATCAACATCGGCTCTGGCCTGGCACTGCTAGGCATGGCG
ACCGTGCTGTGTGACATCATAGTCCTCTACTGCATGAAGAAAAGACTCTACTAT
CGGGAGAAGAAATATAAATATGTGGAAGATTACGAGCAGGGTCTTGCTAGTGA
GCTGGACCAGTGAGGCCTACCAAGCCGAATTC        (SEQ ID NO:21)

FIG. 11

| | | | |
|---|---|---|---|
| humP2X$_4$ | 1 | MAGCCAALAAFLFEYDTPRIVLIRSRKVGLMNR | 33 |
| ratP2X$_4$ | 1 | MAGCCSVLGSFLFEYDTPRIVLIRSRKVGLMNR | 33 |
| humP2X$_4$ | 34 | AVQLLILAYVIGWVFVWEKGYQETDSVVSSVTT | 66 |
| ratP2X$_4$ | 34 | AVQLLILAYVIGWVFVWEKGYQETDSVVSSVTT | 66 |
| humP2X$_4$ | 67 | KVKGVAVTNTSKLGFRIWDVADYVIPAQEENSL | 99 |
| ratP2X$_4$ | 67 | KAKGVAVTNTSQLGFRIWDVADYVIPAQEENSL | 99 |
| humP2X$_4$ | 100 | FVMTNVILTMNQTQGLCPEIPDATTVCKSDASC | 132 |
| ratP2X$_4$ | 100 | FIMTNMIVTVNQTQSTCPEIPDKTSICNSDADC | 132 |
| humP2X$_4$ | 133 | TAGSAGTHSNGVSTGRCVAFNGSVKTCEVAAWC | 165 |
| ratP2X$_4$ | 133 | TPGSVDTHSSGVATGRCVPFNESVKTCEVAAWC | 165 |
| humP2X$_4$ | 166 | PVEDDTHVPQPAFLKAAENFTLLVKNNIWYPKF | 198 |
| ratP2X$_4$ | 166 | PVENDVGVPTPAFLKAAENFTLLVKNNIWYPKF | 198 |
| humP2X$_4$ | 199 | NFSKRNILPNITTTYLKSCIYDAKTDPFCPIFR | 231 |
| ratP2X$_4$ | 199 | NFSKRNILPNITTSYLKSCIYNAQTDPFCPIFR | 231 |

FIG. 12A

| | | | |
|---|---|---|---|
| humP2X₄ | 232 | LGKIVENAGHGFQDMAVEGGIMGIQVNWDCNLD | 264 |
| ratP2X₄ | 232 | LGTIVEDAGHSFQEMAVEGGIMGIQIKWDCNLD | 264 |
| humP2X₄ | 265 | RAASLCLPRYSFRRLDTRDVEHNVSPGYNFRFA | 297 |
| ratP2X₄ | 265 | RAASLCLPRYSFRRLDTRDLEHNVSPGYNFRFA | 297 |
| humP2X₄ | 298 | KYYRDLAGNEQRTLIKAYGIRFDIIVFGKAGKF | 330 |
| ratP2X₄ | 298 | KYYRDLAGKEQRTLTKAYGIRFDIIVFGKAGKF | 330 |
| humP2X₄ | 331 | DIIPTMINIGSGLALLGMATVLCDIIVLYCMKK | 363 |
| ratP2X₄ | 331 | DIIPTMINVGSGLALLGVATVLCDVIVLYCMKK | 363 |
| humP2X₄ | 364 | RLYYREKKYKYVEDYEQGLASELDQ | 388 (SEQ ID NO:22) |
| ratP2X₄ | 364 | KYYYRDKKYKYVEDYEQGLSGEMNQ | 388 (SEQ ID NO:23) |

FIG. 12B

SEQUENCE LISTING

<160> NUMBER OF SEQ ID NOS: 26

<210> SEQ ID NO: 1
<211> LENGTH: 221
<212> TYPE: DNA
<213> ORGANISM: Homo sapiens

<400> SEQUENCE: 1

| | | | | | |
|---|---|---|---|---|---|
| ctcatcaagg | cctacgggat | ccgcattgac | gtcattgtgc | atggacaggc | cgggaagttc | 60 |
| agcctgattc | ccaccattat | taatctggcc | acagctctga | cttccgtcgg | ggtgggctcc | 120 |
| ttcctgtgcg | actggatctt | gctaacattc | atgaacaaaa | acaaggtcta | cagccataag | 180 |
| aaatttgaca | aggtgtgtac | gccgagccac | ccctcaggta | g | | 221 |

<210> SEQ ID NO: 2
<211> LENGTH: 910
<212> TYPE: DNA
<213> ORGANISM: Homo sapiens

<400> SEQUENCE: 2

| | | | | | |
|---|---|---|---|---|---|
| gctcatcaag | gcctacggga | tccgcattga | cgtcattgtg | catggacagg | ccgggaagtt | 60 |
| cagcctgatt | cccaccatta | ttaatctggc | cacagctctg | acttccgtcg | gggtgggctc | 120 |
| cttcctgtgc | gactggatct | tgctaacatt | catgaacaaa | acaaggtct | acagccataa | 180 |
| gaaatttgac | aaggtgtgta | cgccgagcca | cccctcaggt | agctggcctg | tgaccttgc | 240 |
| ccgtgtattg | ggccaggccc | ctcccgaacc | cggccaccgc | tccgaggacc | agcaccccag | 300 |
| ccctccatca | ggccaggagg | gccaacaagg | ggcagagtgt | ggcccagcct | tcccgcccct | 360 |
| gcggccttgc | cccatctctg | ccccttctga | gcagatggtg | gacactcctg | cctccgagcc | 420 |
| tgcccaagcc | tccacaccca | cagaccccaa | aggtttggct | caactctgag | ctccttcca | 480 |
| tctcactgga | ctgcagaccc | ggcctggtgg | ggccagagag | tccccagcta | gggacctgca | 540 |
| cgtggacgtg | gcacctcag | tagcggagca | tctccacgaa | acggggcacc | acaggatccc | 600 |
| tgtgcaaggg | ctgggggcac | gctctggccc | caggcttgtg | ccccacccctg | gcatacagcc | 660 |
| cctgacacct | cctccccagc | tggtccctac | agggctgctc | acttcccatc | acctctcaca | 720 |
| gccacctgga | acccaagcca | gctgagctct | gaggggctct | gctcccggtc | ttgggccctg | 780 |
| ggaaccccac | cccaccccac | cccacaggcg | ttgtaacctc | gaatctgccc | agactcttcc | 840 |
| cttagaagtc | acaacatact | cagtccaata | aacctgtgag | cagaaaaaaa | aaaaaaaaaa | 900 |
| gggcggccgc | | | | | | 910 |

<210> SEQ ID NO: 3
<211> LENGTH: 20
<212> TYPE: DNA
<213> ORGANISM: Homo sapiens

<400> SEQUENCE: 3

| | |
|---|---|
| atgaatgtta gcaagatcca | 20 |

<210> SEQ ID NO: 4
<211> LENGTH: 32
<212> TYPE: DNA
<213> ORGANISM: Homo sapiens

<400> SEQUENCE: 4

| | |
|---|---|
| caucaucauc aucaccccga cggaagtcag ag | 32 |

<210> SEQ ID NO: 5
<211> LENGTH: 20
<212> TYPE: DNA
<213> ORGANISM: Homo sapiens

<400> SEQUENCE: 5
cctgtccatg cacaatgacg 20

<210> SEQ ID NO: 6
<211> LENGTH: 48
<212> TYPE: DNA
<213> ORGANISM: Homo sapiens
<220> FEATURE:
<221> NAME/KEY: modified_base
<222> LOCATION: (36)...(37)
<223> OTHER INFORMATION: n at positions 36 and 37 are I
<220> FEATURE:
<221> NAME/KEY: modified_base
<222> LOCATION: (41)...(42)
<223> OTHER INFORMATION: n at positions 41 and 42 are I
<220> FEATURE:
<221> NAME/KEY: modified_base
<222> LOCATION: (46)...(47)
<223> OTHER INFORMATION: n at positions 46 and 47 are I

<400> SEQUENCE: 6
cuacuacuac uaggccacgc gtcgactagt acgggnnggg nngggnng 48

<210> SEQ ID NO: 7
<211> LENGTH: 32
<212> TYPE: DNA
<213> ORGANISM: Homo sapiens

<400> SEQUENCE: 7
cuacuacuac uaggccacgc gtcgactagt ac 32

<210> SEQ ID NO: 8
<211> LENGTH: 531
<212> TYPE: DNA
<213> ORGANISM: Homo sapiens

<400> SEQUENCE: 8
gaattcggct tctactacta ctaggccacg cgtcgactag tacgggggggg gggggggggg    60 gccccggtgg aagatggggc ctctgtcagc caatttctgg gtacgatggc cccaaatttc   120
gcgatcctca tcaagaacag catccattac cccaaattcc acttctccaa gggcaacatc   180
gccgaccgca cagacgggta cctgaagcgc tgcacgttcc acgaggcctc cgacctttac   240
tgccccatct tcaagctggg cttttatcgtg gagaaggctg gggagagctt cacagagctc   300
gcacacaagg gtggtgtcat cggggtcatt atcaactggg actgtgacct ggacctgcct   360
gcatcggagt gcaaccccaa gtactccttc cggaggcttg accccaagca cgtgcctgcc   420
tcgtcaggct acaacttcag gtttgccaaa tactacaaga tcaatggcac caccacccgc   480
agctcatcaa ggcctacggg atccgcattg acgtcattgt gcatggacag g   531

<210> SEQ ID NO: 9
<211> LENGTH: 24
<212> TYPE: DNA
<213> ORGANISM: Homo sapiens

<400> SEQUENCE: 9
tccttcctgt gcgactggat cttg 24

<210> SEQ ID NO :10
<211> LENGTH: 23
<212> TYPE: DNA
<213> ORGANISM: Homo sapiens

<400> SEQUENCE: 10
caaacctttg gggtctgtgg gtg                                       23

<210> SEQ ID NO: 11
<211> LENGTH: 28
<212> TYPE: DNA
<213> ORGANISM: Homo sapiens

<400> SEQUENCE: 11
ccaccatggc cgccgcccag cccaagta                                  28

<210> SEQ ID NO: 12
<211> LENGTH: 28
<212> TYPE: DNA
<213> ORGANISM: Homo sapiens

<400> SEQUENCE: 12
ggaaaggagc tcagagttga gccaaacc                                  28

<210> SEQ ID NO: 13
<211> LENGTH: 1436
<212> TYPE: DNA
<213> ORGANISM: Homo sapiens

<400> SEQUENCE: 13
ccaccatggc cgccgcccag cccaagtacc ccgccggggc gaccgcccgg cgcctggccc      60
ggggctgctg gtccgccctc tgggactacg agacgcccaa ggtgatcgtg gtgaggaacc     120
ggcgcctggg ggtcctgtac cgcgccgtgc agctgctcat cctgctctac ttcgtgtggt     180
acgtattcat cgtgcagaaa agctaccagg agagcgagac gggccccgag agctccatca     240
tcaccaaggt caagggggatc accacgtccg agcacaaagt gtgggacgtg gaggagtacg     300
tgaagccccc cgagggggggc agcgtgttca gcatcatcac cagggtcgag gccacccact     360
cccagaccca gggaacctgc cccgagagca taagggtcca caacgccacc tgcctctccg     420
acgccgactg cgtggctggg gagctggaca tgctgggaaa cggcctgagg accgggcgct     480
gtgtgcccta ttaccagggg ccctccaaga cctgcgaggt gttcggctgg tgcccggtgg     540
aagatggggc ctctgtcagc caatttctgg gtacgatggc cccaaatttc accatcctca     600
tcaagaacag catccactac cccaaattcc acttctccaa gggcaacatc gccgaccgca     660
cagacgggta cctgaagcgc tgcacgttcc acgaggcctc cgacctctac tgccccatct     720
tcaagctggg cttttatcgtg gagaaggctg gggagagctt cacagagctc gcacacaagg     780
gtggtgtcat cggggtcatt atcaactggg actgtgacct ggacctgcct gcatcggagt     840
gcaaccccaa gtactccttc cggaggcttg accccaagca cgtgcctgcc tcgtcaggct     900
acaacttcag gtttgccaaa tactacaaga tcaatggcac caccacccgc acgctcatca     960
aggcctacgg gatccgcatt gacgtcattg tgcatggaca ggccgggaag ttcagcctga    1020
ttcccaccat tattaatctg gccacagctc tgacttccgt cggggtgggc tccttcctgt    1080
gcgactggat cttgctaaca ttcatgaaca aaaacaaggt ctacagccat aagaaatttg    1140
acaaggtgtg tacgccgagc cacccctcag gtagctggcc tgtgaccctt gcccgtgtat    1200
tgggccaggc ccctcccgaa cccggccacc gctccgagga ccagcacccc agccctccat    1260

```
caggccagga gggccaacaa ggggcagagt gtggcccagc cttccccccc ctgcggcctt    1320
gccccatctc tgcccttct gagcagatgg tggacactcc tgcctccgag cctgcccaag    1380
cctccacacc cacagacccc aaaggtttgg ctcaactctg agctcctttc cgggct       1436

<210> SEQ ID NO: 14
<211> LENGTH: 1421
<212> TYPE: DNA
<213> ORGANISM: Homo sapiens

<400> SEQUENCE: 14
ccaccatggc cgccgcccag cccaagtacc ccgccggggc gaccgcccgg cgcctggccc     60
ggggctgctg gtccgccctc tgggactacg agacgcccaa ggtgatcgtg gtgaggaacc    120
ggcgcctggg ggtcctgtac cgcgccgtgc agctgctcat cctgctctac ttcgtgtggt    180
acgtattcat cgtgcaraaa agctaccagg agagcgagag ggcccccgag agctccatca    240
tcaccaaggt caaggggatc accacgtccg agcacaaagt gtgggacgtg gaggagtacg    300
tgaagccccc cgagggggc agcgtgttca gcatcatcac cagggtcgag gccacccact    360
cccagaccca gggaacctgc cccgagagca taagggtcca caacgccacc tgcctctccg    420
acgccgactg cgtggctggg gagctggaca tgctgggaaa cggcctgagg accgggcgct    480
gtgtgcccta ttaccagggg ccctccaaga cctgcgaggt gttcggctgg tgcccggtgg    540
aagatggggc ctctgtcagc caatttctgg tacgatggc cccaaatttc accatcctca    600
tcaagaacag catccactac cccaaattcc acttctccaa gggcaacatc gccgaccgca    660
cagacgggta cctgaagcgc tgcacgttcc acgaggcctc cgacctctac tgccccatct    720
tcaagctggg ctttatcgtg gagaaggctg gggagagctt cacagagctc gcacacaagg    780
gtggtgtcat cggggtcatt atcaactggg actgtgacct ggacctgcct gcatcggagt    840
gcaaccccaa gtactccttc cggaggcttg accccaagca cgtgcctgcc tcgtcaggct    900
acaacttcag gtttgccaaa tactacaaga tcaatggcac caccacccgc acgtctcatca    960 aggcctacgg gatccgcatt gacgtcattg tgcatggaca ggccgggaag ttcagcctga   1020
ttcccaccat tattaatctg gccacagctc tgacttccgt cggggtgggc tccttcctgt   1080
gcgactggat cttgctaaca ttcatgaaca aaaacaaggt ctacagccat aagaaatttg   1140
acaaggtgtg tacgccgagc caccctcag gtagctggcc tgtgacctt gcccgtgtat   1200 tgggccaggc ccctcccgaa cccggccacc gctccgagga ccagcacccc agccctccat   1260
caggccagga gggccaacaa ggggcagagt gtggcccagc cttcccgccc ctgcggcctt   1320
gccccatctc tgcccttct gagcagatgg tggacactcc tgcctccgag cctgcccaag   1380
cctccacacc cacagacccc aaaggtttgg ctcaactttg a                       1421

<210> SEQ ID NO: 15
<211> LENGTH: 1349
<212> TYPE: DNA
<213> ORGANISM: Homo sapiens

<400> SEQUENCE: 15
ccaccatggc cgccgcccag cccaagtacc ccgccggggc gaccgcccgg cgcctggccc     60
ggggctgctg gtccgccctc tgggactacg agacgcccaa ggtgatcgtg gtgaggaacc    120
ggcgcctggg ggtcctgtac cgcgccgtgc agctgctcat cctgctctac ttcgtgtggt    180
acgtattcat cgtgcagaaa agctaccagg agagcgagac gggcccccgag agctccatca   240
```

-continued

| | |
|---|---|
| tcaccaaggt caaggggatc accacgtccg agcacaaagt gtgggacgtg gaggagtacg | 300 |
| tgaagccccc cgagagcata aggtccaca acgccacctg cctctccgac gccgactgcg | 360 |
| tggctgggga gctggacatg ctgggaaacg gcctgaggac tgggcgctgt gtgccctatt | 420 |
| accaggggcc ctccaagacc tgcgaggtgt tcggctggtg cccggtggaa gatggggcct | 480 |
| ctgtcagcca atttctgggt acgatggccc caaatttcac catcctcatc aagaacagca | 540 |
| tccactaccc caaattccac ttctccaagg gcaacatcgc cgaccgcaca gacgggtacc | 600 |
| tgaagcgctg cacgttccac gaggcctccg acctctactg ccccatcttc aagctgggct | 660 |
| ttatcgtgga gaaggctggg gagagcttca gagctcgc acacaagggt ggtgtcatcg | 720 |
| gggtcattat caactgggac tgtgacctgg acctgcctgc atcggagtgc aaccccaagt | 780 |
| actccttccg gaggcttgac cccaagcacg tgcctgcctc gtcaggctac aacttcaggt | 840 |
| ttgccaaata ctacaagatc aatggcacca ccacccgcac gctcatcaag gcctacggga | 900 |
| tccgcattga cgtcattgtg catggacagg ccgggaagtt cagcctgatt ccaccatta | 960 |
| ttaatctggc cacagctctg acttccgtcg ggtgggctc cttcctgtgc gactggatct | 1020 |
| tgctaacatt catgaacaaa aacaaggtct acagccataa gaaatttgac aaggtgtgta | 1080 |
| cgccgagcca ccctcaggt agctggcctg tgacccttgc ccgtgtattg ggccaggccc | 1140 |
| ctcccgaacc cggccaccgc tccgaggacc agcaccccag ccctcatca ggccaggagg | 1200 |
| gccaacaagg ggcagagtgt ggcccagcct tcccgcccct gcggccttgc ccatctctg | 1260 |
| cccccttctga gcagatggtg gacactcctg cctccgagcc tgcccaagcc tccacacca | 1320 |
| cagaccccaa aggtttggct caactctga | 1349 |

<210> SEQ ID NO: 16
<211> LENGTH: 1499
<212> TYPE: DNA
<213> ORGANISM: Homo sapiens

<400> SEQUENCE: 16

| | |
|---|---|
| ccaccatggc cgccgcccag cccaagtacc ccgccggggc gaccgcccgg cgcctggccc | 60 |
| ggggctgctg gtccgcccctc tgggactacg agacgcccaa ggtgatcgtg gtgaggaacc | 120 |
| ggcgcctggg ggtcctgtac cgcgccgtgc agctgctcat cctgctctac ttcgtgtggt | 180 |
| acgtattcat cgtgcaraaa agctaccagg agagcgagac gggccccgag agctccatca | 240 |
| tcaccaaggt caaggggatc accacgtccg agcacaaagt gtgggacgtg gaggagtacg | 300 |
| tgaagccccc cgaggggggc agcgtgttca gcatcatcac cagggtcgag gccacccact | 360 |
| cccagaccca gggaacctgc cccgagagca taagggtcca caacgccacc tgcctctccg | 420 |
| acgccgactg cgtggctggg gagctggaca tgctgggaaa cggcctgagg accgggcgct | 480 |
| gtgtgcccta ttaccagggg ccctccaaga cctgcgaggt gttcggctgg tgcccggtgg | 540 |
| aagatggggc ctctgtcagc caatttctgg gtacgatggc cccaaatttc accatcctca | 600 |
| tcaagaacag catccactac cccaaattcc acttctccaa gggcaacatc gccgaccgca | 660 |
| cagacgggta cctgaagcgc tgcacgttcc acgaggcctc cgacctctac tgccccatct | 720 |
| tcaagctggg ctttatcgtg gagaaggctg ggagagcttc acagagctc gcacacaagg | 780 |
| gtggtgtcat cggggtcatt atcaactggg actgtgacct ggacctgcct gcatcggagt | 840 |
| gcaaccccaa gtactccttc cggaggcttg accccaagca cgtgcctgcc tcgtcaggct | 900 |
| acaacttcag gtttgccaaa tactacaaga tcaatggcac caccacccgc acgctcatca | 960 |
| aggcctacgg gatccgcatt gacgtcattg tgcatggaca ggccgggaag ttcagcctga | 1020 |

-continued

```
ttcccaccat tattaatctg gccacagctc tgacttccgt cggggtggta aggaaccctc    1080
tctggggtcc cagcgggtgc ggggggtcca ccaggccctt acacaccggt ctctgctggc    1140
cccagggctc cttcctgtgc gactggatct tgctaacatt catgaacaaa aacaaggtct    1200
acagccataa gaaatttgac aaggtgtgta cgccgagcca cccctcaggt agctggcctg    1260
tgacccttgc ccgtgtattg ggccaggccc tcccgaacc cggccaccgc tccgaggacc    1320
agcaccccag ccctccatca ggccaggagg ccaacaagg ggcagagtgt ggcccagcct    1380
tcccgcccct gcggccttgc cccatctctg ccccttctga gcagatggtg gacactcctg    1440
cctccgagcc tgcccaagcc tccacaccca cagaccccaa aggtttggct caactctga    1499
```

<210> SEQ ID NO: 17
<211> LENGTH: 471
<212> TYPE: PRT
<213> ORGANISM: Homo sapiens

<400> SEQUENCE: 17

```
Met Ala Ala Gln Pro Lys Tyr Pro Ala Gly Ala Thr Ala Arg Arg
 1               5                  10                  15

Leu Ala Arg Gly Cys Trp Ser Ala Leu Trp Asp Tyr Glu Thr Pro Lys
             20                  25                  30

Val Ile Val Arg Asn Arg Leu Gly Val Leu Tyr Arg Ala Val
         35                  40                  45

Gln Leu Leu Ile Leu Leu Tyr Phe Val Trp Tyr Val Phe Ile Val Gln
     50                  55                  60

Lys Ser Tyr Gln Glu Ser Glu Thr Gly Pro Glu Ser Ser Ile Ile Thr
 65                  70                  75                  80

Lys Val Lys Gly Ile Thr Thr Ser Glu His Lys Val Trp Asp Val Glu
                 85                  90                  95

Glu Tyr Val Lys Pro Pro Glu Gly Gly Ser Val Phe Ser Ile Ile Thr
                100                 105                 110

Arg Val Glu Ala Thr His Ser Gln Thr Gln Gly Thr Cys Pro Glu Ser
            115                 120                 125

Ile Arg Val His Asn Ala Thr Cys Leu Ser Asp Ala Asp Cys Val Ala
        130                 135                 140

Gly Glu Leu Asp Met Leu Gly Asn Gly Leu Arg Thr Gly Arg Cys Val
145                 150                 155                 160

Pro Tyr Tyr Gln Gly Pro Ser Lys Thr Cys Glu Val Phe Gly Trp Cys
                165                 170                 175

Pro Val Glu Asp Gly Ala Ser Val Ser Gln Phe Leu Gly Thr Met Ala
            180                 185                 190

Pro Asn Phe Thr Ile Leu Ile Lys Asn Ser Ile His Tyr Pro Lys Phe
        195                 200                 205

His Phe Ser Lys Gly Asn Ile Ala Asp Arg Thr Asp Gly Tyr Leu Lys
    210                 215                 220

Arg Cys Thr Phe His Glu Ala Ser Asp Leu Tyr Cys Pro Ile Phe Lys
225                 230                 235                 240

Leu Gly Phe Ile Val Glu Lys Ala Gly Glu Ser Phe Thr Glu Leu Ala
                245                 250                 255

His Lys Gly Gly Val Ile Gly Val Ile Ile Asn Trp Asp Cys Asp Leu
            260                 265                 270

Asp Leu Pro Ala Ser Glu Cys Asn Pro Lys Tyr Ser Phe Arg Arg Leu
        275                 280                 285
```

```
Asp Pro Lys His Val Pro Ala Ser Ser Gly Tyr Asn Phe Arg Phe Ala
    290                 295                 300

Lys Tyr Tyr Lys Ile Asn Gly Thr Thr Arg Thr Leu Ile Lys Ala
305                 310                 315                 320

Tyr Gly Ile Arg Ile Asp Val Ile Val His Gly Gln Ala Gly Lys Phe
                325                 330                 335

Ser Leu Ile Pro Thr Ile Ile Asn Leu Ala Thr Ala Leu Thr Ser Val
            340                 345                 350

Gly Val Gly Ser Phe Leu Cys Asp Trp Ile Leu Leu Thr Phe Met Asn
            355                 360                 365

Lys Asn Lys Val Tyr Ser His Lys Lys Phe Asp Lys Val Cys Thr Pro
    370                 375                 380

Ser His Pro Ser Gly Ser Trp Pro Val Thr Leu Ala Arg Val Leu Gly
385                 390                 395                 400

Gln Ala Pro Pro Glu Pro Gly His Arg Ser Glu Asp Gln His Pro Ser
                405                 410                 415

Pro Pro Ser Gly Gln Glu Gly Gln Gln Gly Ala Glu Cys Gly Pro Ala
            420                 425                 430

Phe Pro Pro Leu Arg Pro Cys Pro Ile Ser Ala Pro Ser Glu Gln Met
            435                 440                 445

Val Asp Thr Pro Ala Ser Glu Pro Ala Gln Ala Ser Thr Pro Thr Asp
    450                 455                 460

Pro Lys Gly Leu Ala Gln Leu
465                 470

<210> SEQ ID NO: 18
<211> LENGTH: 404
<212> TYPE: PRT
<213> ORGANISM: Homo sapiens

<400> SEQUENCE: 18

Met Ala Ala Ala Gln Pro Lys Tyr Pro Ala Gly Ala Thr Ala Arg Arg
  1                 5                  10                  15

Leu Ala Arg Gly Cys Trp Ser Ala Leu Trp Asp Tyr Glu Thr Pro Lys
                20                  25                  30

Val Ile Val Val Arg Asn Arg Arg Leu Gly Val Leu Tyr Arg Ala Val
            35                  40                  45

Gln Leu Leu Ile Leu Leu Tyr Phe Val Trp Tyr Val Phe Ile Val Gln
50                  55                  60

Lys Ser Tyr Gln Glu Ser Glu Thr Gly Pro Glu Ser Ser Ile Ile Thr
65                  70                  75                  80

Lys Val Lys Gly Ile Thr Thr Ser Glu His Lys Val Trp Asp Val Glu
                85                  90                  95

Glu Tyr Val Lys Pro Pro Glu Gly Gly Ser Val Phe Ser Ile Ile Thr
            100                 105                 110

Arg Val Glu Ala Thr His Ser Gln Thr Gln Gly Thr Cys Pro Glu Ser
        115                 120                 125

Ile Arg Val His Asn Ala Thr Cys Leu Ser Asp Ala Asp Cys Val Ala
    130                 135                 140

Gly Glu Leu Asp Met Leu Gly Asn Gly Leu Arg Thr Gly Arg Cys Val
145                 150                 155                 160

Pro Tyr Tyr Gln Gly Pro Ser Lys Thr Cys Glu Val Phe Gly Trp Cys
                165                 170                 175

Pro Val Glu Asp Gly Ala Ser Val Ser Gln Phe Leu Gly Thr Met Ala
            180                 185                 190
```

```
Pro Asn Phe Thr Ile Leu Ile Lys Asn Ser Ile His Tyr Pro Lys Phe
            195                 200                 205

His Phe Ser Lys Gly Asn Ile Ala Asp Arg Thr Asp Gly Tyr Leu Lys
            210                 215                 220

Arg Cys Thr Phe His Glu Ala Ser Asp Leu Tyr Cys Pro Ile Phe Lys
225                 230                 235                 240

Leu Gly Phe Ile Val Glu Lys Ala Gly Glu Ser Phe Thr Glu Leu Ala
                245                 250                 255

His Lys Gly Gly Val Ile Gly Val Ile Ile Asn Trp Asp Cys Asp Leu
            260                 265                 270

Asp Leu Pro Ala Ser Glu Cys Asn Pro Lys Tyr Ser Phe Arg Arg Leu
            275                 280                 285

Asp Pro Lys His Val Pro Ala Ser Ser Gly Tyr Asn Phe Arg Phe Ala
290                 295                 300

Lys Tyr Tyr Lys Ile Asn Gly Thr Thr Thr Arg Thr Leu Ile Lys Ala
305                 310                 315                 320

Tyr Gly Ile Arg Ile Asp Val Ile Val His Gly Gln Ala Gly Lys Phe
                325                 330                 335

Ser Leu Ile Pro Thr Ile Ile Asn Leu Ala Thr Ala Leu Thr Ser Val
            340                 345                 350

Gly Val Gly Ser Phe Leu Cys Asp Trp Ile Leu Leu Thr Phe Met Asn
            355                 360                 365

Lys Asn Lys Val Tyr Ser His Lys Lys Phe Asp Lys Met Val Asp Thr
370                 375                 380

Pro Ala Ser Glu Pro Ala Gln Ala Ser Thr Pro Thr Asp Pro Lys Gly
385                 390                 395                 400

Leu Ala Gln Leu

<210> SEQ ID NO: 19
<211> LENGTH: 447
<212> TYPE: PRT
<213> ORGANISM: Homo sapiens

<400> SEQUENCE: 19

Met Ala Ala Ala Gln Pro Lys Tyr Pro Ala Gly Ala Thr Ala Arg Arg
  1               5                  10                  15

Leu Ala Arg Gly Cys Trp Ser Ala Leu Trp Asp Tyr Glu Thr Pro Lys
                20                  25                  30

Val Ile Val Val Arg Asn Arg Leu Gly Val Leu Tyr Arg Ala Val
            35                  40                  45

Gln Leu Leu Ile Leu Leu Tyr Phe Val Trp Tyr Val Phe Ile Val Gln
    50                  55                  60

Lys Ser Tyr Gln Glu Ser Glu Thr Gly Pro Glu Ser Ser Ile Ile Thr
65                  70                  75                  80

Lys Val Lys Gly Ile Thr Thr Ser Glu His Lys Val Trp Asp Val Glu
                85                  90                  95

Glu Tyr Val Lys Pro Pro Glu Ser Ile Arg Val His Asn Ala Thr Cys
                100                 105                 110

Leu Ser Asp Ala Asp Cys Val Ala Gly Glu Leu Asp Met Leu Gly Asn
            115                 120                 125

Gly Leu Arg Thr Gly Arg Cys Val Pro Tyr Tyr Gln Gly Pro Ser Lys
        130                 135                 140

Thr Cys Glu Val Phe Gly Trp Cys Pro Val Glu Asp Gly Ala Ser Val
145                 150                 155                 160
```

-continued

```
Ser Gln Phe Leu Gly Thr Met Ala Pro Asn Phe Thr Ile Leu Ile Lys
                165                 170                 175

Asn Ser Ile His Tyr Pro Lys Phe His Phe Ser Lys Gly Asn Ile Ala
            180                 185                 190

Asp Arg Thr Asp Gly Tyr Leu Lys Arg Cys Thr Phe His Glu Ala Ser
        195                 200                 205

Asp Leu Tyr Cys Pro Ile Phe Lys Leu Gly Phe Ile Val Glu Lys Ala
    210                 215                 220

Gly Glu Ser Phe Thr Glu Leu Ala His Lys Gly Gly Val Ile Gly Val
225                 230                 235                 240

Ile Ile Asn Trp Asp Cys Asp Leu Asp Leu Pro Ala Ser Glu Cys Asn
                245                 250                 255

Pro Lys Tyr Ser Phe Arg Arg Leu Asp Pro Lys His Val Pro Ala Ser
                260                 265                 270

Ser Gly Tyr Asn Phe Arg Phe Ala Lys Tyr Tyr Lys Ile Asn Gly Thr
            275                 280                 285

Thr Thr Arg Thr Leu Ile Lys Ala Tyr Gly Ile Arg Ile Asp Val Ile
        290                 295                 300

Val His Gly Gln Ala Gly Lys Phe Ser Leu Ile Pro Thr Ile Ile Asn
305                 310                 315                 320

Leu Ala Thr Ala Leu Thr Ser Val Gly Val Gly Ser Phe Leu Cys Asp
                325                 330                 335

Trp Ile Leu Leu Thr Phe Met Asn Lys Asn Lys Val Tyr Ser His Lys
                340                 345                 350

Lys Phe Asp Lys Val Cys Thr Pro Ser His Pro Ser Gly Ser Trp Pro
            355                 360                 365

Val Thr Leu Ala Arg Val Leu Gly Gln Ala Pro Pro Glu Pro Gly His
        370                 375                 380

Arg Ser Glu Asp Gln His Pro Ser Pro Ser Gly Gln Glu Gly Gln
385                 390                 395                 400

Gln Gly Ala Glu Cys Gly Pro Ala Phe Pro Leu Arg Pro Cys Pro
                405                 410                 415

Ile Ser Ala Pro Ser Glu Gln Met Val Asp Thr Pro Ala Ser Glu Pro
            420                 425                 430

Ala Gln Ala Ser Thr Pro Thr Asp Pro Lys Gly Leu Ala Gln Leu
        435                 440                 445

<210> SEQ ID NO: 20
<211> LENGTH: 497
<212> TYPE: PRT
<213> ORGANISM: Homo sapiens

<400> SEQUENCE: 20

Met Ala Ala Gln Pro Lys Tyr Pro Ala Gly Ala Thr Ala Arg Arg
  1               5                  10                  15

Leu Ala Arg Gly Cys Trp Ser Ala Leu Trp Asp Tyr Glu Thr Pro Lys
            20                  25                  30

Val Ile Val Val Arg Asn Arg Arg Leu Gly Val Leu Tyr Arg Ala Val
        35                  40                  45

Gln Leu Leu Ile Leu Leu Tyr Phe Val Trp Tyr Val Phe Ile Val Gln
    50                  55                  60

Lys Ser Tyr Gln Glu Ser Glu Thr Gly Pro Glu Ser Ser Ile Ile Thr
65                  70                  75                  80

Lys Val Lys Gly Ile Thr Thr Ser Glu His Lys Val Trp Asp Val Glu
```

```
                         85                  90                  95
Glu Tyr Val Lys Pro Pro Glu Gly Ser Val Phe Ser Ile Ile Thr
                100                 105                 110
Arg Val Glu Ala Thr His Ser Gln Thr Gln Gly Thr Cys Pro Glu Ser
                115                 120                 125
Ile Arg Val His Asn Ala Thr Cys Leu Ser Asp Ala Asp Cys Val Ala
            130                 135                 140
Gly Glu Leu Asp Met Leu Gly Asn Gly Leu Arg Thr Gly Arg Cys Val
145                 150                 155                 160
Pro Tyr Tyr Gln Gly Pro Ser Lys Thr Cys Glu Val Phe Gly Trp Cys
                165                 170                 175
Pro Val Glu Asp Gly Ala Ser Val Ser Gln Phe Leu Gly Thr Met Ala
            180                 185                 190
Pro Asn Phe Thr Ile Leu Ile Lys Asn Ser Ile His Tyr Pro Lys Phe
                195                 200                 205
His Phe Ser Lys Gly Asn Ile Ala Asp Arg Thr Asp Gly Tyr Leu Lys
            210                 215                 220
Arg Cys Thr Phe His Glu Ala Ser Asp Leu Tyr Cys Pro Ile Phe Lys
225                 230                 235                 240
Leu Gly Phe Ile Val Glu Lys Ala Gly Glu Ser Phe Thr Glu Leu Ala
                245                 250                 255
His Lys Gly Gly Val Ile Gly Val Ile Ile Asn Trp Asp Cys Asp Leu
            260                 265                 270
Asp Leu Pro Ala Ser Glu Cys Asn Pro Lys Tyr Ser Phe Arg Arg Leu
            275                 280                 285
Asp Pro Lys His Val Pro Ala Ser Ser Gly Tyr Asn Phe Arg Phe Ala
        290                 295                 300
Lys Tyr Tyr Lys Ile Asn Gly Thr Thr Thr Arg Thr Leu Ile Lys Ala
305                 310                 315                 320
Tyr Gly Ile Arg Ile Asp Val Ile Val His Gly Gln Ala Gly Lys Phe
                325                 330                 335
Ser Leu Ile Pro Thr Ile Ile Asn Leu Ala Thr Ala Leu Thr Ser Val
            340                 345                 350
Gly Val Val Arg Asn Pro Leu Trp Gly Pro Ser Gly Cys Gly Gly Ser
            355                 360                 365
Thr Arg Pro Leu His Thr Gly Leu Cys Trp Pro Gln Gly Ser Phe Leu
    370                 375                 380
Cys Asp Trp Ile Leu Leu Thr Phe Met Asn Lys Asn Lys Val Tyr Ser
385                 390                 395                 400
His Lys Lys Phe Asp Lys Val Cys Thr Pro Ser His Pro Ser Gly Ser
                405                 410                 415
Trp Pro Val Thr Leu Ala Arg Val Leu Gly Gln Ala Pro Pro Glu Pro
            420                 425                 430
Gly His Arg Ser Glu Asp Gln His Pro Ser Pro Ser Gly Gln Glu
            435                 440                 445
Gly Gln Gln Gly Ala Glu Cys Gly Pro Ala Phe Pro Leu Arg Pro
    450                 455                 460
Cys Pro Ile Ser Ala Pro Ser Glu Gln Met Val Asp Thr Pro Ala Ser
465                 470                 475                 480
Glu Pro Ala Gln Ala Ser Thr Pro Thr Asp Pro Lys Gly Leu Ala Gln
                485                 490                 495
Leu
```

<210> SEQ ID NO: 21
<211> LENGTH: 1206
<212> TYPE: DNA
<213> ORGANISM: Homo sapiens

<400> SEQUENCE: 21

```
gaattcggct tgcgccacc atggcgggct gctgcgccgc gctggcggcc ttcctgttcg      60
agtacgacac gccgcgcatc gtgctcatcc gcagccgcaa agtgggctc atgaaccgcg     120
ccgtgcaact gctcatcctg gcctacgtca tcgggtgggt gtttgtgtgg gaaaagggct     180
accaggaaac tgactccgtg gtcagctccg ttacgaccaa ggtcaagggc gtggctgtga     240
ccaacacttc taaacttgga ttccggatct gggatgtggc ggattatgtg ataccagctc     300
aggaggaaaa ctcccctctt gtcatgacca acgtgatcct caccatgaac cagacacagg     360
gcctgtgccc cgagattcca gatgcgacca ctgtgtgtaa atcagatgcc agctgtactg     420
ccggctctgc cggcacccac agcaacggag tctcaacagg caggtgcgta gctttcaacg     480
ggtccgtcaa gacgtgtgag gtggcggcct ggtgcccggt ggaggatgac acacacgtgc     540
cacaacctgc tttttaaag gctgcagaaa acttcactct tttggttaag aacaacatct     600
ggtatcccaa atttaatttc agcaagagga atatccttcc caacatcacc actacttacc     660
tcaagtcgtg catttatgat gctaaaacag atcccttctg ccccatattc cgtcttggca     720
aaatagtgga gaacgcagga cacggttttc caggacatgg cgtggaggga ggcatcatgg     780
gcatccaggt caactgggac tgcaacctgg acagagccgc ctcccctctgc ttgcccaggt     840
actccttccg ccgcctcgat acacgggacg ttgagcacaa cgtatctcct ggctacaatt     900
tcaggtttgc caagtactac agagacctgg ctggcaacga gcagcgcacg ctcatcaagg     960
cctatggcat ccgcttcgac atcattgtgt ttgggaaggc agggaaattt gacatcatcc    1020
ccactatgat caacatcggc tctggcctgg cactgctagg catggcgacc gtgctgtgtg    1080
acatcatagt cctctactgc atgaagaaaa gactctacta tcgggagaag aaatataaat    1140
atgtggaaga ttcgagcag ggtcttgcta gtgagctgga ccagtgaggc ctaccaagcc    1200
gaattc                                                              1206
```

<210> SEQ ID NO: 22
<211> LENGTH: 388
<212> TYPE: PRT
<213> ORGANISM: Homo sapiens

<400> SEQUENCE: 22

```
Met Ala Gly Cys Cys Ala Ala Leu Ala Ala Phe Leu Phe Glu Tyr Asp
 1               5                  10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
    50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Glu Glu
                85                  90                  95

Asn Ser Leu Phe Val Met Thr Asn Val Ile Leu Thr Met Asn Gln Thr
            100                 105                 110
```

Gln Gly Leu Cys Pro Glu Ile Pro Asp Ala Thr Thr Val Cys Lys Ser
            115                 120                 125

Asp Ala Ser Cys Thr Ala Gly Ser Ala Gly Thr His Ser Asn Gly Val
130                 135                 140

Ser Thr Gly Arg Cys Val Ala Phe Asn Gly Ser Val Lys Thr Cys Glu
145                 150                 155                 160

Val Ala Ala Trp Cys Pro Val Glu Asp Thr His Val Pro Gln Pro
            165                 170                 175

Ala Phe Leu Lys Ala Ala Glu Asn Phe Thr Leu Leu Val Lys Asn Asn
            180                 185                 190

Ile Trp Tyr Pro Lys Phe Asn Phe Ser Lys Arg Asn Ile Leu Pro Asn
            195                 200                 205

Ile Thr Thr Thr Tyr Leu Lys Ser Cys Ile Tyr Asp Ala Lys Thr Asp
            210                 215                 220

Pro Phe Cys Pro Ile Phe Arg Leu Gly Lys Ile Val Glu Asn Ala Gly
225                 230                 235                 240

His Gly Phe Gln Asp Met Ala Val Glu Gly Ile Met Gly Ile Gln
            245                 250                 255

Val Asn Trp Asp Cys Asn Leu Asp Arg Ala Ala Ser Leu Cys Leu Pro
            260                 265                 270

Arg Tyr Ser Phe Arg Arg Leu Asp Thr Arg Asp Val Glu His Asn Val
            275                 280                 285

Ser Pro Gly Tyr Asn Phe Arg Phe Ala Lys Tyr Tyr Arg Asp Leu Ala
            290                 295                 300

Gly Asn Glu Gln Arg Thr Leu Ile Lys Ala Tyr Gly Ile Arg Phe Asp
305                 310                 315                 320

Ile Ile Val Phe Gly Lys Ala Gly Lys Phe Asp Ile Ile Pro Thr Met
            325                 330                 335

Ile Asn Ile Gly Ser Gly Leu Ala Leu Leu Gly Met Ala Thr Val Leu
            340                 345                 350

Cys Asp Ile Ile Val Leu Tyr Cys Met Lys Lys Arg Leu Tyr Tyr Arg
            355                 360                 365

Glu Lys Lys Tyr Lys Tyr Val Glu Asp Tyr Glu Gln Gly Leu Ala Ser
            370                 375                 380

Glu Leu Asp Gln
385

<210> SEQ ID NO: 23
<211> LENGTH: 388
<212> TYPE: PRT
<213> ORGANISM: Rattus rattus

<400> SEQUENCE: 23

Met Ala Gly Cys Cys Ser Val Leu Gly Ser Phe Leu Phe Glu Tyr Asp
1               5                   10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
            35                  40                  45

Val Trp Glu Lys Gly Tyr Gln Glu Thr Asp Ser Val Val Ser Ser Val
            50                  55                  60

Thr Thr Lys Ala Lys Gly Val Ala Val Thr Asn Thr Ser Gln Leu Gly
65                  70                  75                  80

Phe Arg Ile Trp Asp Val Ala Asp Tyr Val Ile Pro Ala Gln Glu Glu
            85                  90                  95

```
Asn Ser Leu Phe Ile Met Thr Asn Met Ile Val Thr Val Asn Gln Thr
            100                 105                 110

Gln Ser Thr Cys Pro Glu Ile Pro Asp Lys Thr Ser Ile Cys Asn Ser
        115                 120                 125

Asp Ala Asp Cys Thr Pro Gly Ser Val Asp Thr His Ser Ser Gly Val
    130                 135                 140

Ala Thr Gly Arg Cys Val Pro Phe Asn Glu Ser Val Lys Thr Cys Glu
145                 150                 155                 160

Val Ala Ala Trp Cys Pro Val Glu Asn Asp Val Gly Val Pro Thr Pro
                165                 170                 175

Ala Phe Leu Lys Ala Ala Glu Asn Phe Thr Leu Leu Val Lys Asn Asn
                180                 185                 190

Ile Trp Tyr Pro Lys Phe Asn Phe Ser Lys Arg Asn Ile Leu Pro Asn
            195                 200                 205

Ile Thr Thr Ser Tyr Leu Lys Ser Cys Ile Tyr Asn Ala Gln Thr Asp
        210                 215                 220

Pro Phe Cys Pro Ile Phe Arg Leu Gly Thr Ile Val Glu Asp Ala Gly
225                 230                 235                 240

His Ser Phe Gln Glu Met Ala Val Glu Gly Gly Ile Met Gly Ile Gln
                245                 250                 255

Ile Lys Trp Asp Cys Asn Leu Asp Arg Ala Ala Ser Leu Cys Leu Pro
            260                 265                 270

Arg Tyr Ser Phe Arg Arg Leu Asp Thr Arg Asp Leu Glu His Asn Val
        275                 280                 285

Ser Pro Gly Tyr Asn Phe Arg Phe Ala Lys Tyr Tyr Arg Asp Leu Ala
    290                 295                 300

Gly Lys Glu Gln Arg Thr Leu Thr Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Val Gly Ser Gly Leu Ala Leu Leu Gly Val Ala Thr Val Leu
            340                 345                 350

Cys Asp Val Ile Val Leu Tyr Cys Met Lys Lys Tyr Tyr Tyr Arg
        355                 360                 365

Asp Lys Lys Tyr Lys Tyr Val Glu Asp Tyr Glu Gln Gly Leu Ser Gly
    370                 375                 380

Glu Met Asn Gln
385

<210> SEQ ID NO: 24
<211> LENGTH: 145
<212> TYPE: DNA
<213> ORGANISM: Artificial Sequence
<220> FEATURE:
<223> OTHER INFORMATION: primer

<400> SEQUENCE: 24
gcgggnccat ggcgggctgc tgcgccgcgc tggngcccct tcctgttcga gtacgacacg      60
ccgcgcatcg tgctcatccg cagccgcaaa gtggggctca tgaaccgcgc cgtgcaactg     120
ctcatcctgg cctacgtcat cgggt                                           145

<210> SEQ ID NO: 25
<211> LENGTH: 32
<212> TYPE: DNA
<213> ORGANISM: Artificial Sequence
```

-continued

```
<220> FEATURE:
<223> OTHER INFORMATION: primer (sense)

<400> SEQUENCE: 25
gcgccaccat ggcgggctgc tgcgccgcgc tg                              32

<210> SEQ ID NO: 26
<211> LENGTH: 32
<212> TYPE: DNA
<213> ORGANISM: Artificial Sequence
<220> FEATURE:
<223> OTHER INFORMATION: primer (antisense)

<400> SEQUENCE: 26
ggtaggcctc actggtccag ctcactagca ag                              32
```

NUCLEIC ACIDS ENCODING A FUNCTIONAL HUMAN PURINORECEPTOR P2X2 AND P2X4, AND METHODS OF PRODUCTION AND USE THEREOF

This application is a continuation-in-part of Ser. No. 09/137,458 filed on Aug. 20, 1998 and also claims priority to provisional application Ser. No. 60/065,822 filed Nov. 14, 1997.

TECHNICAL FIELD

The invention relates generally to receptor proteins and to DNA and RNA molecules encoding therefor. In particular, the invention relates to a nucleic acid sequence that encodes a human receptor $P2X_2$ and $P2X_4$. The invention also relates to methods of using the receptors encoded thereby to identify compounds that interact with them. This invention further relates to compounds which act as antagonists and agonists to compounds which have reactivity with the various P2X receptor and methods utilized in determining said reactivity. The invention also involves therapeutic uses involving aspects of these receptors.

BACKGROUND OF THE INVENTION

P2 receptors have been generally categorized as either metabotropic nucleotide receptors or ionotropic receptors for extracellular nucleotides. Metabotropic nucleotide receptors (usually designated P2Y or $P2Y_n$, where "n" is a subscript integer indicating subtype) are believed to differ from ionotropic receptors (usually designated P2X or $P2X_n$) in that they are based on a different fundamental means of transmembrane signal transduction: P2Y receptors operate through a G protein-coupled system, while P2X receptors are ligand-gated ion channels. The ligand for these P2X receptors is ATP, and/or other natural nucleotides, for example, ADP, UTP, UDP, or synthetic nucleotides, for example 2-methylthioATP.

At least seven P2X receptors, and the cDNA sequences encoding them, have been identified to date. $P2X_1$ cDNA was cloned from the smooth muscle of the rat vas deferens (Valera et al (1994) Nature 371:516–519) and $P2X_2$ cDNA was cloned from PC12 cells (Brake et al. (1994) Nature 371:519–523). Five other P2X receptors have been found in cDNA libraries by virtue of their sequence similarity to $P2X_1$ and $P2X_2$ ($P2X_3$: Lewis et al. (1995) Nature 377:432–435, Chen et al. (1995) Nature 377:428–431; $P2X_4$: Buell et al. (1996) EMBO J. 15:55–62, Seguela et al. (1996) J. Neurosci. 16:448–455, Bo et al. (1995) FEBS Lett. 375:129–133, Soto et al. (1996) Proc. Natl. Acad. Sci. USA 93:3684–3688, Wang et al. (1996) Biochem. Biophys. Res. Commun.220:196–202; $P2X_5$: Collo et al. (1996) J. Neurosci. 16:2495–2507, Garcia-Guzman et al. (1996) FEBS Lett. 388:123–127; $P2X_6$: Collo et al. (1996), supra, Soto et al. (1996) Biochem. Biophys. Res. Commun. 223:456–460; $P2X_7$: Surprenant et al. (1996) Science 272:735–738). For a comparison of the amino acid sequences of rat P2X receptors see Buell et al. (1996) Eur. J. Neurosci. 8:2221–2228.

Native P2X receptors form rapidly activated, nonselective cationic channels that are activated by ATP. Rat $P2X_1$ and rat $P2X_2$ have equal permeability to $Na^+$ and $K^+$ but significantly less to $Cs^+$. The channels formed by the P2X receptors generally have high $Ca^{2+}$ permeability ($P_{Ca}/P_{Na} \cong 4$). The cloned rat $P2X_1$, $P2X_2$ and $P2X_4$ receptors exhibit the same permeability for $Ca^{2+}$ observed with native receptors. However, the mechanism by which P2X receptors form an ionic pore or bind ATP is not known.

A variety of tissues and cell types, including epithelial, immune, muscle and neuronal, express at least one form of P2X receptor. The widespread distribution of $P2X_4$ receptors in the rat central nervous system suggests a role for $P2X_4$-mediated events in the central nervous system. However, study of the role of individual P2X receptors is hampered by the lack of receptor subtype-specific agonists and antagonists. For example, one agonist useful for studying ATP-gated channels is $\alpha,\beta$-methylene-ATP ($\alpha,\beta$meATP). However, the P2X receptors display differential sensitivity to the agonist with $P2X_1$ and $P2X_2$ being $\alpha,\beta$meATP-sensitive and insensitive, respectively. Furthermore, binding of $\alpha,\beta$meATP to P2X receptors does not always result in channel opening. The predominant forms of P2X receptors in the rat brain, $P2X_4$ and $P2X_6$ receptors, cannot be blocked by suramin or PPADS. These two forms of the P2X receptor are also not activated by $\alpha,\beta$meATP and are, thus, intractable to study with currently available pharmacological tools.

A therapeutic role for P2 receptors has been suggested, for example, for cystic fibrosis (Boucher et al. (1995) in: Belardinelli et al. (eds) Adenosine and Adenine Nucleotides: From Molecular Biology to Integrative Physiology (Kluwer Acad., Norwell Mass.) pp 525–532), diabetes (Loubatiéres-Mariani et al. (1995) in: Belardinelli et al. (eds), supra, pp 337–345), immune and inflammatory diseases (Di Virgilio et al. (1995) in: Belardinelli et al. (eds), supra, pp 329–335), cancer (Rapaport (1993) Drug Dev. Res. 28:428–431), constipation and diarrhea (Milner et al. (1994) in: Kamm et al. (eds.) Constipation and Related Disorders: Pathophysiology and Management in Adults and Children (Wrightson Biomedical, Bristol) pp 41–49), behavioral disorders such as epilepsy, depression and aging-associated degenerative diseases (Williams (1993) Drug. Dev. Res. 28:438–444), contraception and sterility (Foresta et al. (1992) J. Biol. Chem. 257:19443–19447), and wound healing (Wang et al. (1990) Biochim. Biophys. Res. Commun. 166:251–258).

Accordingly, there is a need in the art for specific agonists and antagonists for each P2X receptor subtype and, in particular, agents that will be effective in vivo, as well as for methods for identifying P2X receptor-specific agonist and antagonist compounds.

SUMMARY OF THE INVENTION

The present invention relates to human $P2X_2$ and $P2X_4$ receptors.

In one embodiment, a DNA molecule or fragments thereof is provided, wherein the DNA molecule encodes aforementioned human P2X receptors, or subunits thereof.

In another embodiment, a recombinant vector comprising such DNA molecules, or fragments thereof, is provided.

In another embodiment, the subject invention is directed to a human $P2X_2$ and $P2X_4$ receptor polypeptides, either alone or in multimeric form.

In still other embodiments, the invention is directed to messenger RNA encoded by the DNA, recombinant host cells transformed or transfected with vectors comprising the DNA or fragments thereof, and methods of producing recombinant P2X polypeptides using such cells.

In yet another embodiment, the invention is directed to a method of expressing the above human P2X receptors, or a subunit thereof, in a cell to produce the resultant P2X-containing receptors.

In a further embodiment, the invention is directed to a method of using such cells to identify potentially therapeutic compounds that modulate or otherwise interact with the above P2X-containing receptors.

In another embodiment, therapeutic uses involving P2X modulators, such as an ATP agonist or antagonist are contemplated.

These and other embodiments of the present invention will readily occur to those of ordinary skill in the art in view of the disclosure herein.

BRIEF DESCRIPTION OF THE DRAWINGS

FIG. 1 depicts the partial sequence of a cDNA clone (SEQ ID NO:1) derived from human fetal colon tissue which encodes a polypeptide with homology to a region of the rat $P2X_2$ receptor;

FIG. 2 depicts the full sequence of the cDNA clone (SEQ ID NO:2), the underlined sequences sequence denotes overlap with the sequence of FIG. 1;

FIGS. 3a–e depicts primers designed to the cDNA of FIG. 2 and commercial RACE primers: 3a depicts GSP 1 (SEQ ID NO:3); 3b depicts GSP 2 (SEQ ID NO:4); 3c depicts GSP 3 (SEQ ID NO:5); 3d depicts the anchor primer (SEQ ID NO:6); and 3e depicts the universal amplification primer (SEQ ID NO:7);

FIG. 4 depicts the approximately 600 bp product (SEQ ID NO:8) produced by 5' RACE reactions using poly A RNA from human pituitary tissue;

FIGS. 5a and b depicts genomic primers (SEQ ID NO:9 and SEQ ID NO:10);

FIGS. 6a and b depicts $hP2X_2$ RT-PCR primers (SEQ ID NO:11 and SEQ ID NO:12);

FIG. 7a–d depicts four species of cDNAs (SEQ ID NO:13; SEQ ID NO:14; SEQ ID NO:15; and SEQ ID NO:16, respectively) containing intact open reading frames from the predicted initiation to termination sites;

FIGS. 8a–d depicts the predicted amino acid sequences (SEQ ID NO:17; SEQ ID NO:18; SEQ ID NO:19; and SEQ ID NO:20) encoded by the nucleotides of FIG. 7;

FIG. 9 depicts an alignment of the predicted amino acid sequences (SEQ ID NO:17; SEQ ID NO:18; SEQ ID NO:19; and SEQ ID NO:20); and FIG. 10 depicts electrophysiological characterization of $hP2X_2$ channels.

FIG. 11 depicts the sequence of the intact open reading frame of the human $P2X_4$ receptor (SEQ ID NO:21). The EcoRI sites used in subcloning are underlined and the start (ATG) and stop (TGA) codons of the open reading frame (ORF) are shaded.

FIG. 12A and FIG. 12B are the aligned predicted amino acid sequences of the human ($humP2X_4$) (SEQ ID NO:22) and rat (rat $P2X_4$) (SEQ ID NO: 23) receptors. Identical residues are shaded.

DETAILED DESCRIPTION OF THE INVENTION

The practice of the present invention will employ, unless otherwise indicated, conventional techniques of molecular biology, microbiology, recombinant DNA technology, electrophysiology, and pharmacology, that are within the skill of the art. Such techniques are explained fully in the literature. See, for example, Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press).

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

In describing the present invention, the following terms will be employed, and are intended to be defined as indicated below.

The term "P2 receptor" intends a purinergic receptor for the ligand ATP and/or other purine or pyrimidine nucleotides, whether natural or synthetic. P2 receptors are broadly subclassified as "P2X" or "P2Y" receptors. These types differ in their pharmacology, structure, and signal transduction mechanisms. The P2X receptors are generally ligand-gated ion channels, while the P2Y receptors operate generally through a G protein-coupled system. Moreover, and without intending to be limited by theory, it is believed that P2X receptors comprise multimers of receptor polypeptides, which multimers may be of either the same or different subtypes. Consequently, the term "P2X receptor" refers, as appropriate, to the individual receptor subunit or subunits, as well as to the homomeric and heteromeric receptors comprised thereby.

The term "$P2X_n$" intends a P2X receptor subtype wherein n is an integer of at least 1. At the time of the invention, at least 7 $P2X_n$ receptor subtypes have been isolated and/or characterized.

A "$P2X_2$ receptor agonist" is a compound that binds to and activates a $P2X_2$ receptor. Similarly, a "$P2X_4$ receptor agonist is a compound that binds to and activates a $P2X_4$ receptor. By "activates" is intended the elicitation of one or more pharmacological, physiological, or electrophysiological responses. Such responses may include, but are not limited to, an increase in receptor-specific cellular depolarization.

A "$P2X_2$ receptor antagonist" is a substance that binds to a $P2X_2$ receptor and prevents agonists from activating the receptor. Similarly, a "$P2X_4$ receptor antagonist", is a substance that binds to a $P2X_4$ receptor and prevents agonists from activating its corresponding receptor. Pure antagonists do not activate the receptor, but some substances may have mixed agonist and antagonist properties.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as by methylation and/or by capping, and unmodified forms of the polynucleotide.

The term "variant" is used to refer to an oligonucleotide sequence which differs from the related wild-type sequence in the insertion, deletion or substitution of one or more nucleotides. When not caused by a structurally conservative mutation (see below), such a variant oligonucleotide is expressed as a "protein variant" which, as used herein, indicates a polypeptide sequence that differs from the wild-type polypeptide in the insertion, deletion or substitution of one or more amino acids. The protein variant differs in primary structure (amino acid sequence), but may or may not differ significantly in secondary or tertiary structure or in function relative to the wild-type.

The term "mutant" generally refers to an organism or a cell displaying a new genetic character or phenotype as the result of change in its gene or chromosome. In some instances, however, "mutant" may be used in reference to a variant protein or oligonucleotide and "mutation" may refer to the change underlying the variant.

"Polypeptide" and "protein" are used interchangeably herein and indicate a molecular chain of amino acids linked through peptide bonds. The terms do not refer to a specific length of the product. Thus, peptides, oligopeptides, and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide, provided that such fragments, etc. retain the binding or other characteristics necessary for their intended use.

A "functionally conservative mutation" as used herein intends a change in a polynucleotide encoding a derivative polypeptide in which the activity is not substantially altered compared to that of the polypeptide from which the derivative is made. Such derivatives may have, for example, amino acid insertions, deletions, or substitutions in the relevant molecule that do not substantially affect its properties. For example, the derivative can include conservative amino acid substitutions, such as substitutions which preserve the general charge, hydrophobicity/hydrophilicity, side chain moiety, and/or steric bulk of the amino acid substituted, for example, Gly/Ala, Val/Ile/Leu, Asp/Glu, Lys/Arg, Asn/Gln, Thr/Ser, and Phe/Trp/Tyr.

By the term "structurally conservative mutant" is intended a polynucleotide containing changes in the nucleic acid sequence but encoding a polypeptide having the same amino acid sequence as the polypeptide encoded by the polynucleotide from which the degenerate variant is derived. This can occur because a specific amino acid may be encoded by more than one "codon," or sequence of three nucleotides, i.e., because of the degeneracy of the genetic code.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected. Cells in primary culture as well as cells such as oocytes also can be used as recipients.

A "vector" is a replicon in which another polynucleotide segment is attached, such as to bring about the replication and/or expression of the attached segment. The term includes expression vectors, cloning vectors, and the like.

A "coding sequence" is a polynucleotide sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art. See, for example, Sambrook et al., supra; DNA Cloning, Vols. I and II, supra; Nucleic Acid Hybridization, supra.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences. A coding sequence may be operably linked to control sequences that direct the transcription of the polynucleotide whereby said polynucleotide is expressed in a host cell.

The term "transfection" refers to the insertion of an exogenous polynucleotide into a host cell, irrespective of the method used for the insertion, or the molecular form of the polynucleotide that is inserted. The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome. "Transfection" generally is used in reference to a eukaryotic cell while the term "transformation" is used to refer to the insertion of a polynucleotide into a prokaryotic cell. "Transformation" of a eukaryotic cell also may refer to the formation of a cancerous or tumorigenic state.

The term "isolated," when referring to a polynucleotide or a polypeptide, intends that the indicated molecule is present in the substantial absence of other similar biological macromolecules. The term "isolated" as used herein means that at least 75 wt. %, more preferably at least 85 wt. %, more preferably still at least 95 wt. %, and most preferably at least 98 wt. % of a composition is the isolated polynucleotide or polypeptide. An "isolated polynucleotide" that encodes a particular polypeptide refers to a polynucleotide that is substantially free of other nucleic acid molecules that do not encode the subject polypeptide; however, the molecule may include functionally and/or structurally conservative mutations as defined herein.

A "test sample" as used herein intends a component of an individual's body which is a source of one of the P2X receptors, including $P2X_2$ and $P2X_4$. These test samples include biological samples which can be evaluated by the methods of the present invention described herein and include body fluids such as whole blood, tissues and cell preparations.

The following single-letter amino acid abbreviations are used throughout the text:

Alanine A
Arginine R
Asparagine N
Aspartic acid D
Cysteine C
Glutamine Q
Glutamic acid E
Glycine G Histidine H
Isoleucine I
Leucine L
Lysine K
Methionine M
Phenylalanine F
Proline P
Serine S
Threonine T
Tryptophan W
Tyrosine Y
Valine V Human $P2X_2$ and $P2X_4$ receptors, polynucleotides encoding variant receptors or polypeptide subunits thereof, and methods of making these receptors are provided herein. The invention includes not only the above P2X receptors but also methods for screening compounds using the receptor and cells expressing the receptor. Further, polynucleotides and antibodies which can be used in methods for detection of the receptor, as well as the reagents useful in these methods, are provided. Compounds and polynucleotides useful in regulating the receptor and its expression also are provided as disclosed hereinbelow.

In one preferred embodiment, the polynucleotide encodes the aforementioned human P2X receptor polypeptides or protein variants thereof containing conservative amino acid substitutions.

DNA encoding the above mentioned human P2X receptors, and variants thereof, can be derived from genomic or cDNA, prepared by synthesis, or by a combination of techniques. The DNA can then be used to express the human P2X receptor or as a template for the preparation of RNA using methods well known in the art (see, Sambrook et al., supra), or as a molecular probe capable of selectively hybridizing to, and therefore detecting the presence of, other P2X-encoding nucleotide sequences.

cDNA encoding the $P2X_2$ and $P2X_4$ receptors may be obtained from an appropriate DNA library. cDNA libraries may be probed using the procedure described by Grunstein et al. (1975) Proc. Natl. Acad. Sci. USA 73:3961. The cDNA thus obtained can then be modified and amplified using the polymerase chain reaction ("PCR") and primer sequences to obtain the specific DNA encoding the human P2X receptor.

More particularly, PCR employs short oligonucleotide primers (generally 10–20 nucleotides in length) that match opposite ends of a desired sequence within the DNA molecule. The sequence between the primers need not be known. The initial template can be either RNA or DNA. If RNA is used, it is first reverse transcribed to cDNA. The cDNA is then denatured, using well-known techniques such as heat, and appropriate oligonucleotide primers are added in molar excess.

Primer extension is effected using DNA polymerase in the presence of deoxynucleotide triphosphates or nucleotide analogs. The resulting product includes the respective primers at their 5'-termini, covalently linked to the newly synthesized complements of the original strands. The replicated molecule is again denatured, hybridized with primers, and so on, until the product is sufficiently amplified. Such PCR methods are described in for example, U.S. Pat. Nos. 4,965,188; 4,800,159; 4,683,202; 4,683,195; incorporated herein by reference in their entireties. The product of the PCR is cloned and the clones containing the P2X receptor DNA, derived by segregation of the primer extended strand, selected. Selection can be accomplished using a primer as a hybridization probe.

Alternatively still, the respective P2X receptor DNA could be generated using an RT-PCR (reverse transcriptase—polymerase chain reaction) approach starting with human RNA. Human RNA may be obtained from cells or tissue in which the specific P2X receptor is expressed, for example, brain, spinal cord, uterus or lung, using conventional methods. For example, single-stranded cDNA is synthesized from human RNA as the template using standard reverse transcriptase procedures and the cDNA is amplified using PCR. This is but one example of the generation of P2X receptor variants from a human tissue RNA template. Reverse transcription of human RNAs can also be accomplished utiilzing reagents from the Superscript Preamplification System (GibcoBRL, Gaithersburg, Md.) and the following method: Poly A+RNA (1 microgram) derived from pituitary gland tissue (Clontech, Inc. Palo Alto, Calif.) and 1 $\mu$l (50 nanograms) random hexamer primers are combined in a final volume of 12 $\mu$l $dH_2O$. This mixture is heated to 70° C. for 10 minutes and chilled on ice for 1 minute. The following components are added: 2 $\mu$l 10×PCR buffer (200 mM Tris-HCl pH 8.4, 500 mM KCl), 2 $\mu$l 25 mM $MgCl_2$, 1 $\mu$l 10 mM dNTP mix, and 2 $\mu$l 0.1 M dithiothreitol. The reaction is equilibrated for 5 minutes at 25° C. after which 1 $\mu$l (200 units) Superscript II reverse transcriptase is added and incubation continued at 25° C. for 10 minutes, followed by 50 minutes at 42° C. Alternatively, 10 picomoles Oligo dT primer can be substituted for the random hexamer primers in the above reaction mixture. In this case, equilibration is carried out at 42° C. for 2 minutes after which the reverse transcriptase is added and incubation continued at 42° C. for 50 minutes. The reverse transcription reaction is terminated by incubation at 70° C. for 15 minutes and chilled on ice. Rnase H (1 $\mu$l; 2 units) is added and the mixture incubated for 20 minutes at 37° C., then stored on ice.

Synthetic oligonucleotides may be prepared using an automated oligonucleotide synthesizer such as that described by Warner (1984) DNA 3:401. If desired, the synthetic strands may be labeled with $^{32}$P by treatment with polynucleotide kinase in the presence of $^{32}$P-ATP, using standard conditions for the reaction. DNA sequences, including those isolated from genomic or cDNA libraries, may be modified by known methods which include site-directed mutagenesis as described by Zoller (1982) Nucleic Acids Res. 10:6487. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned. Alternatively, it may be necessary to identify clones by sequence analysis if there is difficulty in distinguishing the variant from wild type by hybridization. In any case, the DNA would be sequence-confirmed.

Once produced, DNA encoding the specific P2X receptor may then be incorporated into a cloning vector or an expression vector for replication in a suitable host cell. Vector construction employs methods known in the art.

Generally, site-specific DNA cleavage is performed by treating with suitable restriction enzymes under conditions that generally are specified by the manufacturer of these commercially available enzymes. After incubation with the restriction enzyme, protein is removed by extraction and the DNA recovered by precipitation. The cleaved fragments may be separated using, for example, polyacrylamide or agarose gel electrophoresis methods, according to methods known by those of skill in the art.

Sticky end cleavage fragments may be blunt ended using E. coli DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Alternatively, restriction enzyme digestion of unwanted fragments can be used to prevent ligation.

Standard vector constructions generally include specific antibiotic resistance elements. Ligation mixtures are transformed into a suitable host, and successful transformants selected by antibiotic resistance or other markers. Plasmids from the transformants can then be prepared according to methods known to those in the art usually following a chloramphenicol amplification as reported by Clewell et al. (1972) J. Bacteriol. 110:667. The DNA is isolated and analyzed usually by restriction enzyme analysis and/or sequencing. Sequencing may be by the well-known dideoxy method of Sanger et al. (1977) Proc. Natl. Acad. Sci. USA 74:5463) as further described by Messing et al. (1981) Nucleic Acid Res. 9:309, or by the method reported by Maxam et al. (1980) Meth. Enzymol. 65:499. Problems with band compression, which are sometimes observed in GC rich regions, are overcome by use of, for example, T-deazoguanosine or inosine, according to the method reported by Barr et al. (1986) Biotechniques 4:428.

Host cells are genetically engineered with the vectors of this invention, which may be a cloning vector or an expression vector. The vector may be in the form of a plasmid, a viral particle, a phage, etc. The engineered host cells can be cultured in conventional nutrient media modified as appropriate for activating promoters, selecting transformants/transfectants or amplifying the subunit-encoding polynucleotide. The culture conditions, such as temperature, pH and the like, generally are similar to those previously used with the host cell selected for expression, and will be apparent to those of skill in the art.

Both prokaryotic and eukaryotic host cells may be used for expression of desired coding sequences when appropriate control sequences that are compatible with the designated host are used. For example, among prokaryotic hosts, Escherchia coli is frequently used. Also, for example, expression control sequences for prokaryotes include but are not limited to promoters, optionally containing operator portions, and ribosome binding sites. Transfer vectors compatible with prokaryotic hosts can be derived from, for example, the plasmid pBR322 that contains operons conferring ampicillin and tetracycline resistance, and the various pUC vectors, that also contain sequences conferring antibiotic resistance markers. These markers may be used to obtain successful transformants by selection. Commonly used prokaryotic control sequences include but are not limited to the lactose operon system (Chang et al. (1977) Nature 198:1056), the tryptophan operon system (reported by Goeddel et al. (1980) Nucleic Acid Res. 8:4057) and the lambda-derived Pl promoter and N gene ribosome binding site (Shimatake et al. (1981) Nature 292:128), the hybrid Tac promoter (De Boer et al. (1983) Proc. Natl. Acad. Sci. USA 292:128) derived from sequences of the trp and lac UV5 promoters. The foregoing systems are particularly compatible with E. coli; however, other prokaryotic hosts such as strains of Bacillus or Pseudomonas may be used if desired.

Eukaryotic hosts include yeast and mammalian cells in culture systems. *Pichia pastors, Saccharomyces cerevisiae* and *S. carlsbergensis* are commonly used yeast hosts. Yeast-compatible vectors carry markers that permit selection of successful transformants by conferring protrophy to auxotrophic mutants or resistance to heavy metals on wild-type strains. Yeast-compatible vectors may employ the 2-$\mu$ origin of replication (Broach et al. (1983) Meth. Enzymol. 101:307), the combination of CEN3 and ARS1 or other means for assuring replication, such as sequences that will result in incorporation of an appropriate fragment into the host cell genome. Control sequences for yeast vectors are known in the art and include but are not limited to promoters for the synthesis of glycolytic enzymes, including the promoter for 3-phosphoglycerate kinase. See, for example, Hess et al. (1968) J. Adv. Enzyme Reg. 7:149, Holland et al. (1978) Biochemistry 17:4900 and Hitzeman (1980) J. Biol. Chem. 255:2073. For example, some useful control systems are those that comprise the glyceraldehyde-3-phosphate dehydrogenase (GAPDH) promoter or alcohol dehydrogenase (ADH) regulatable promoter, or the hybrid yeast promoter ADH2/GAPDH described in Cousens et al. Gene (1987) 61:265–275, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and are available from depositories such as the American Type Culture Collection. These include but are not limited to HeLa cells, human embryonic kidney (HEK) cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV) and cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which ensure integration of the appropriate sequences encoding the P2X receptors into the host genome. An example of such a mammalian expression system is described in Gopalakrishnan et al. (1995), Eur. J. Pharmacol.-Mol. Pharmacol. 290: 237–246.

Other eukaryotic systems are also known, as are methods for introducing polynucleotides into such systems, such as amphibian cells, using standard methods such as described in Briggs et al. (1995) Neuropharmacol. 34:583–590 or St ühmer (1992) Meth. Enzymol. 207:319–345, insect cells using methods described in Summers and Smith, Texas Agricultural Experiment Station Bulletin No. 1555 (1987), and the like.

The baculovirus expression system can be used to generate high levels of recombinant proteins in insect host cells. This system allows for high level of protein expression, while post-translationally processing the protein in a manner similar to mammalian cells. These expression systems use viral promoters that are activated following baculovirus infection to drive expression of cloned genes in the insect cells (O'Reilly et al. (1992) Baculovirus Expression Vectors: A Laboratory Manual, IRL/Oxford University Press).

Transfection may be by any known method for introducing polynucleotides into a host cell, including packaging the polynucleotide in a virus and transducing a host cell with the virus, by direct uptake of the polynucleotide by the host cell, and the like, which methods are known to those skilled in the art. The transfection procedures selected depend upon the host to be transfected and are determined by the rountineer.

The expression of the receptor may be detected by use of a radioligand selective for the receptor. However, any radioligand binding technique known in the art may be used to detect the receptor (see, for example, Winzor et al. (1995) Quantitative Characterization of Ligand Binding, Wiley-Liss, Inc., NY;

Michel et al. (1997) Mol. Pharmacol. 51:524–532). Alternatively, expression can be detected by utilizing antibodies or functional measurements, i.e., ATP-stimulated cellular depolarization using methods that are well known to those skilled in the art. For example, agonist-stimulated $Ca^{2+}$influx, or inhibition by antagonists of agonist-stimulated $Ca^{2+}$influx, can be measured in mammalian cells transfected with the recombinant $P2X_2$ receptor cDNA, such as COS, CHO or HEK cells. Alternatively, $Ca^{2+}$influx can be measured in cells that do not naturally express P2 receptors, for example, the 1321N1 human astrocytoma cell line, have been prepared using recombinant technology to transiently or stably express the $P2X_2$ and $P2X_4$ receptors.

The P2X polypeptides are recovered and purified from recombinant host cell cultures expressing the same by known methods including ammonium sulfate or ethanol precipitation, acid extraction, anion or cation exchange chromatography, phosphocellulose chromatography, hydrophobic interaction chromatography, hydroxyapatite chromatography or lectin chromatography. Protein refolding steps can be used, as necessary, in completing configuration of the protein. Finally, high performance liquid chromatography (HPLC) can be employed for final purification steps.

The human P2X receptor polypeptides, or fragments thereof, of the present invention also may be synthesized by conventional techniques known in the art, for example, by chemical synthesis such as solid phase peptide synthesis. In general, these methods employ either solid or solution phase synthesis methods. See, for example, J. M. Stewart and J. D. Young, Solid Phase Peptide Synthesis, 2nd Ed., Pierce Chemical Co., Rockford, Ill. (1984) and G. Barany and R. B. Merrifield, The Peptides: Analysis, Synthesis, Biology, editors E. Gross and J. Meienhofer, Vol. 2, Academic Press, New York, (1980), pp. 3–254, for solid phase peptide synthesis techniques; and M. Bodansky, Principles of Peptide Synthesis, Springer-Verlag, Berlin (1984) and E. Gross and J. Meienhofer, Eds., The Peptides: Analysis, Synthesis, Biology, supra, Vol. 1, for classical solution synthesis.

In one preferred system, either the DNA or the RNA derived therefrom, each of which encode the specific human P2X receptor, may be expressed by direct injection into a cell, such as a Xenopus laevis oocyte. Using this method, the functionality of the human $P2X_2$ and/or $P2X_4$ receptor encoded by the DNA or the mRNA can be evaluated as follows. A receptor-encoding polynucleotide is injected into an oocyte for translation into a functional receptor subunit. The function of the expressed variant human $P2X_2$ and/or $P2X_4$ receptor can be assessed in the oocyte by a variety of techniques including electrophysiological techniques such as voltage-clamping, and the like.

Receptors expressed in a recombinant host cell may be used to identify compounds that modulate $P2X_2$ and $P2X_4$ activity. In this regard, the specificity of the binding of a compound showing affinity for the receptor is demonstrated by measuring the affinity of the compound for cells expressing the receptor or membranes from these cells. This may be done by measuring specific binding of labeled (for example, radioactive) compound to the cells, cell membranes or isolated receptor, or by measuring the ability of the compound to displace the specific binding of a standard labeled ligand. See, Michel et al., supra. Expression of variant receptors and screening for compounds that bind to, or inhibit the binding of labeled ligand to these cells or membranes, provide a method for rapid selection of compounds with high affinity for the receptor. These compounds may be agonists, antagonists or modulators of the receptor.

Expressed receptors also may be used to screen for compounds that modulate P2X receptor activity. One method for identifying compounds that modulate P2X activity, comprises providing a cell that expresses a specific human P2X receptor polypeptide, combining a test compound with the cell and measuring the effect of the test compound on that P2X receptor activity. The cell may be a bacterial cell, a mammalian cell, a yeast cell, an amphibian cell, an insect or any other cell expressing the receptor. Preferably, the cell is a mammalian cell or an amphibian cell. Thus, for example, a test compound is evaluated for its ability to elicit an appropriate response, for example, the stimulation of cellular depolarization, or for its ability to modulate the response to an agonist or antagonist.

Additionally, compounds capable of modulating P2X receptors are considered potential therapeutic agents in several disorders including, without limitation, central nervous system or peripheral nervous system conditions, for example, epilepsy, pain, depression, neurodegenerative diseases, and the like, and in disorders of skeletal muscle such as neuromuscular diseases.

In addition, the DNA, or RNA derived therefrom, can be used to design oligonucleotide probes for DNAs that express specific P2X receptors. As used herein, the term "probe" refers to a structure comprised of a polynucleotide, as defined above, which contains a nucleic acid sequence complementary to a nucleic acid sequence present in a target polynucleotide. The polynucleotide regions of probes may be composed of DNA, and/or RNA, and/or synthetic nucleotide analogs. Such probes could be useful in in vitro hybridization assays to distinguish $P2X_2$ and $P2X_4$ variants from wild-type message, with the proviso that it may be difficult to design a method capable of making such a distinction given the small differences that may exist between sequences coding the wild-type and a variant P2X receptor. Alternatively, a PCR-based assay could be used to amplify the sample RNA or DNA for sequence analysis.

Furthermore, each specific P2X polypeptide or fragment (s) thereof can be used to prepare monoclonal antibodies using techniques that are well known in the art. The specific P2X receptor or relevant fragments can be obtained using the recombinant technology outlined below, i.e., a recombinant cell that expresses the receptor or fragments can be cultured to produce quantities of the receptor or fragment that can be recovered and isolated. Alternatively, the specific P2X polypeptide or fragment(s) thereof can be synthesized using conventional polypeptide synthetic techniques as known in the art. Monoclonal antibodies that display specificity and selectivity for a particular P2X polypeptide can be labeled with a measurable and detectable moiety, for example, a fluorescent moiety, radiolabels, enzymes, chemiluminescent labels and the like, and used in in vitro assays. It is theorized that such antibodies could be used to identify wild-type or variant P2X receptor polypeptides for immunodiagnostic purposes. For example, antibodies have been generated to detect amyloid b1-40 v. 1-42 in brain tissue (Wisniewski et al. (1996) Biochem. J. 313:575–580; also see, Suzuki et al. (1994) Science 264:1336–1340; Gravina et al. (1995) J. Biol. Chem. 270:7013–7016; and Turnet et al. (1996) J. Biol. Chem. 271:8966–8970).

Therapeutic Indications for Modulators of the Human $P2X_2$ Receptor

Activation of the $P2X_2$ receptor by ATP and other nucleotides regulates ion gradients across the cell membrane, modulates the cytosolic concentrations of cations, including Ca2+, Na+ and K+, and has a role in the regulation of cell membrane potential which in turn has specific physiological effects.

Pain

The rat $P2X_2$ receptor is expressed in the spinal cord, and in the nodose and dorsal root ganglia (Brake et al., Nature 371:519–523 (1994)), a distribution consistent with a role in pain transmission. Specifically, the $P2X_2$ receptor subunit forms functional channels when expressed alone, and it can also form a functional heteromultimeric channel that has properties similar to currents seen in native sensory channels when co-expressed with the $P2X_3$ receptor, another P2X receptor which is expressed in sensory neurons (Lewis et al., Nature 377:432–435 (1995)). Evidenced from studies in rat nodose ganglia indicate that both $P2X_2/P2X_3$ heteromeric channels and $P2X_2$ homomeric channels contribute to ATP currents (Virginio et al., J. Physiol (Lone) 510:27–35 (1998); Thomas, et al., J. Physiol (Lond) 509 (Pt 2):411–417 (1998)). ATP, which activates $P2X_2$ and $P2X_2/P2X_3$ receptors, functions as an excitatory neurotransmitter in the spinal cord dorsal horn and in primary afferents from sensory ganglia (Holton and Holton, J. Physiol. (Lond) 126:124–140 (1954)). ATP-induced activation of P2X receptors on dorsal root ganglion nerve terminals in the spinal cord stimulates the release of glutamate, a key neurotransmitter involved in nociceptive signaling (Gu and MacDermott, Nature 389:749–753 (1997)). Thus, ATP released from damaged cells evokes pain by activating $P2X_2$ or $P2X_2/P2X_3$ receptors on nociceptive nerve endings or sensory nerves. This is consistent with the induction of pain by intradermally applied ATP in the human blister-base model (Bleehen, Br J. Pharmacol 62:573–577 (1978)), and with reports that P2X receptor antagonists are analgesic in animal models (Driessen and Starke, Naunyn Schmiederbergs Arch Pharmacol 350:618–625 (1994)). This evidence clearly suggests that $P2X_2$ functions in nociception, and that modulators of the human $P2X_2$ receptor are useful as analgesics.

Thus, compounds which block or inhibit activation of $P2X_2$ receptors serve to block the pain stimulus. Antagonists to compounds which normally activate the $P2X_2$ receptor, such as ATP, could successfully block the transmission of pain.

Diseases of the Neuroendocrine System

Extracellular ATP induces secretion of hormones, including prolactin and leuteinizing hormone, from cells of the pituitary gland (Chen et al., Proc Natl Acad Sci USA 92:5219–5223 (1995); Nunez et al, Am J. Physiol 272:E1117–E1123 (1997)). (Carew et al., Cell Calcium 16:227–235 (1994)) (Villalobos et al., Am J Physiol 273:C1963–C1971 (1997)). In addition, since ATP is co-released with hormones such as insulin, prolactin, and leuteinizing hormone, as well as with catecholamines from adrenal chromaffin cells, it may act as a paracrine regulator of hormone release in these tissues (Chen et al., Proc Natl Acad Sci USA 92:5219:5223 (1995); Tomic et al., J Biol Chem 271:21200–21208 (1996); Nunez et al., Am J Physiol 272:E1171–E1123 (1997)) (Leitner et al., Endocrinology 96:662–677 (1975)); Hollins and Ikeda, J Neurophysiol 78:3069–3076 (1997)). The human $P2X_2$ receptor has been found in neuroendocrine tissue and, specifically, the human $P2X_2$ receptor cDNAs was cloned from pituitary tissue RNA. In addition, the $P2X_2$ receptor RNA and protein have been detected in rat pituitary tissue (Brake et al., Nature 371:519–523 (1994)) (Housley et al., Biochem Biophys Res Commun 212:501–508 (1995); Tomic et al., J Biol Chem 271:21200–21208 (1996); Vulchanova et al., Proc Natl Acad Sci USA 93:8063–8067 (1996)). Clearly, the $P2X_2$ receptor is involved in hormone secretion via activation by ATP. Thus, an agonist or antagonist to ATP would be effective in modulating hormone release. Thus, pharmaceutical agents that act on the $P2X_2$ receptor may be useful to modulate hormonal secretion from this gland.

Auditory and Vestibular Disorders

Extracellular ATP acts as a stimulus for neurons and epithelial cells of the inner ear (Housley, Mol Neurobial 16:2148 (1998)). Perfusion of ATP into the guinea pig cochlear perilymphatic compartment inhibits auditory parameters such as auditory-nerve compound action potential and sound tranduction current across the apical surface of sensory hair cells. (Bobbin and Thompson, Ann Otol Rhinol Laryngol 87:185–190 (1978)). Perfusion of ATP into the cochlear endolymph also inhibits sensory current transduction and endocochlear potential, and these effects are blocked by the P2 receptor antagonists suramin and reactive blue 2 (Munoz et al., Hear Res 90:119–125 (1995)). Suramin also blocks the decline in quadratic electrophysiological and mechanical coupling of the organ of Corti which occurs during continuous sound stimulation, suggesting that P2 activation plays a role in this event (Kujawa et al., Hear Res 78:181–188 (1994); (Housley, Mol Neurogiol 16:21–48 (1998)).

ATP also affects vestibular system function. ATP stimulates vestibular afferent nerve discharge, and these responses are blocked by the P2 antagonist suramin and reactive blue 2 (Aubert et al., Neuroscience 62–963–974 (1994);

Aubert et al., Neuroscience 64:1153–1160 (1995)).

Autoradiographic binding studies using ATP analogs indicate the presence of P2 receptors on auditory tissues (Mockett et al., Hear Res 84:177–193 (1995)). $P2X_2$ receptor messenger RNA has been localized in tissues of the rat auditory system. Several message variants for this receptor have been found in various vestibular and auditory tissues, including the cochlea, spiral ganglia, Dieter's cells, christa ampullaris, and the organ of Corti (Glowatzki et al., Proc R Soc Lond B Biol Sci 262:141–147 (1995); Housley et al., Biochem Biophys Res Commun 212:501–508 (1995); Salih et al., Neuroreport 9:279–282 (1998); Chen and Bobbin, Br J Pharmacol 124:337–344 (1998); Housley et al., J Comp Neurol 393:403–414 (1998)). Evidence of the expression of $P2X_2$ receptors in those tissues of the auditory and vestibular systems which are functionally modulated by ATP indicates a role for this receptor in auditory and vestibular function. Altered function of P2 receptors in the ear have pathological implications, as exposure to noise has been shown to alter the response of outer hair cells to ATP (Chen et al., Hear Res 88:215–221(1995)), and $P2X_2$ receptor modulators may have utility in disorders of auditory and vestibular function. Thus, ATP agonists and antagonists have effects on modulation of the $P2X_2$ receptor, in auditory and vestibular functions.

Other

ATP is a potent neurotransmitter in neurons of the gastrointestinal tract, and ATP-mediated signals from enteric neurons appears to be characteristic of $P2X_2$ receptors (Zhou and Galligan, J Physiol (Lond) 496 (Pt 3):719–729 (1996)). Additionally, the discovery of the human $P2X_2$ EST from a library derived from colon tissue suggests that this receptor plays a role in gastrointestinal function. $P2X_2$ is also expressed in vascular smooth muscle tissue, where ATP has been shown to influence vascular tone (Nori et al., J. Vasc Res 35:179–185 (1998)) (Kennedy et al., Eur J Pharmacol 107:161–168 (1985)).

The rat $P2X_6$ receptor message has been found to be expressed in a variety of central nervous system tissues, and the distribution of this receptor parallels that of the rat $P2X_4$ receptor (Collo et al., J. Neuroscience 16:2495–2507 (1996)). These two P2X subtypes can interact to form heteromeric receptors with novel pharmacologic properties (Ll et al., J. Neuroscience. 18:7152–7159 receptors could be a target for pharmaceutical intervention in diseases of the central nervous system.

A recent study identified an mRNA identical to the human $P2X_6$ receptor described herein which is expressed at high levels in skeletal muscle (Urano et al. Cancer Res. 57:3281–3287 (1997)). Additionally, this gene is inducible by the p53 tumor suppressor gene product, suggesting that the human $P2X_6$ receptor plays a role in skeletal muscle cell proliferation and/or differentiation. Therefore, agents that modulate the activity of this receptor may be useful as therapeutics for musculoskeletal disorders such as sarcomas.

Further $P2X_4$ receptors are heavily distributed in the central nervous system (CNS), especially in brain and spinal cord. This strongly indicates that $P2X_4$ receptors may play a role in psychiatric disorders such as depression. Therefore, $P2X_4$ modulators may play a role in treating such disorders.

Below are examples of specific embodiments for carrying out the present invention. The examples are offered for illustrative purposes only, and are not intended to limit the scope of the present invention in any way.

EXAMPLE 1
Identification of a Human cDNA Sequence Likely to Encode $P2X_2$ Polypeptide The predicted amino acid sequence of the rat $P2X_2$ receptor (Genbank accession number 1352688) was used to search for human DNA sequences which would code for similar polypeptides. The TBLASTN database search tool (Altschul (1993) J. Mol. Evol. 36:290–300) was used, which allows querying nucleotide databases with a protein sequence by dynamically translating the DNA sequences into all 6 possible reading frames. A search of the Lifeseq database (Incyte Pharmaceuticals, Inc., Palo Alto California, Calif.) revealed a partial sequence of cDNA clone derived from human fetal colon tissue which encoded a polypeptide having a high degree of homology to a region of the rat $P2X_2$ receptor. The database entry for this sequence is shown in FIG. 1 and SEQ. ID NO:1.

The position of this sequence with respect to that of the rat $P2X_2$ sequence predicted that this cDNA clone would only contain a partial coding sequence for the receptor. The cDNA clone was ordered and the clone was fully sequenced as shown in FIG. 2 and SEQ ID NO:2. Note that in FIG. 2 the underlined sequence denotes overlap with the original database entry.

Primers were designed to the non-coding sequence of this cDNA to enable 5' RACE procedures in an attempt to identify the missing coding sequence, shown in FIG. 3 and SEQ.ID. NOS:3–7. Using poly A plus RNA derived from human pituitary tissue, 5' RACE reactions were performed using a commercially available system (GibcoBRL, Gaithersburg, Md.). A product of approximately 600 bp was cloned and sequenced, shown in FIG. 4 and SEQ ID NO:8. This product was found to contain additional sequence information for an open reading frame with homology to the P2X receptors, but did not extend to what would be the predicted initiation codon of an intact receptor cDNA. A pair of primers were designed and synthesized based on the sequence compiled from Incyte clone 1310493 and the RACE product, and are shown in FIG. 5. These primers were sent to Genome Systems (St. Louis, Mo.) and used in PCR reactions to probe a P1 bacteriophage library of human genomic DNA. Two clones were identified and obtained from Genome systems. The human $P2X_2$ gene contained in clone 18860 was sequenced both directly and after subcloning into the vector pBluescript II SK+.

EXAMPLE 2
Isolation of Human cDNAs Encoding Novel P2 Receptors

Using information on the sequence surrounding the predicted initiation and termination codons of the human $P2X_2$ message, oligonucleotide primers were designed and synthesized to enable RT-PCR of the intact open reading frame of the mRNA. The sequence of these primers, $hP2X_2$ 5' and $hP2X_2$ 3', are shown in FIG. 6. The primers were used to amplify the open reading frames of human $P2X_2$ receptors in reverse transcription- PCR reactions as follows: Poly A+ RNA (1 microgram) derived from pituitary gland tissue (Clontech, Inc. Palo Alto, Calif.) and 10 picomoles oligo dT primer were combined in a final volume of 12 µl $dH_2O$. This mixture was heated to 70° C. for 10 min. and chilled on ice for 1 min. The following components were added: 2 µl 10X PCR buffer (200 mM Tris-HCl pH 8.4, 500 mM KCl), 2 µl 25 mM $MgCl_2$, 1 µl 10 mM dNTP mix, and 2 µl 0.1M dithiothreitol. The reaction was equilibrated to 42° C. for 2 minutes after which 1 µl (200 units) Superscript II reverse transcriptase was added and incubation continued at 42° C. for 50 minutes. The reaction was terminated by incubation at 70° C. for 15 min. and chilled on ice. Rnase H (1 µl; 2 units) was added and the mixture was incubated for 20 minutes at 37° C., then stored on ice.

Figure 9B:
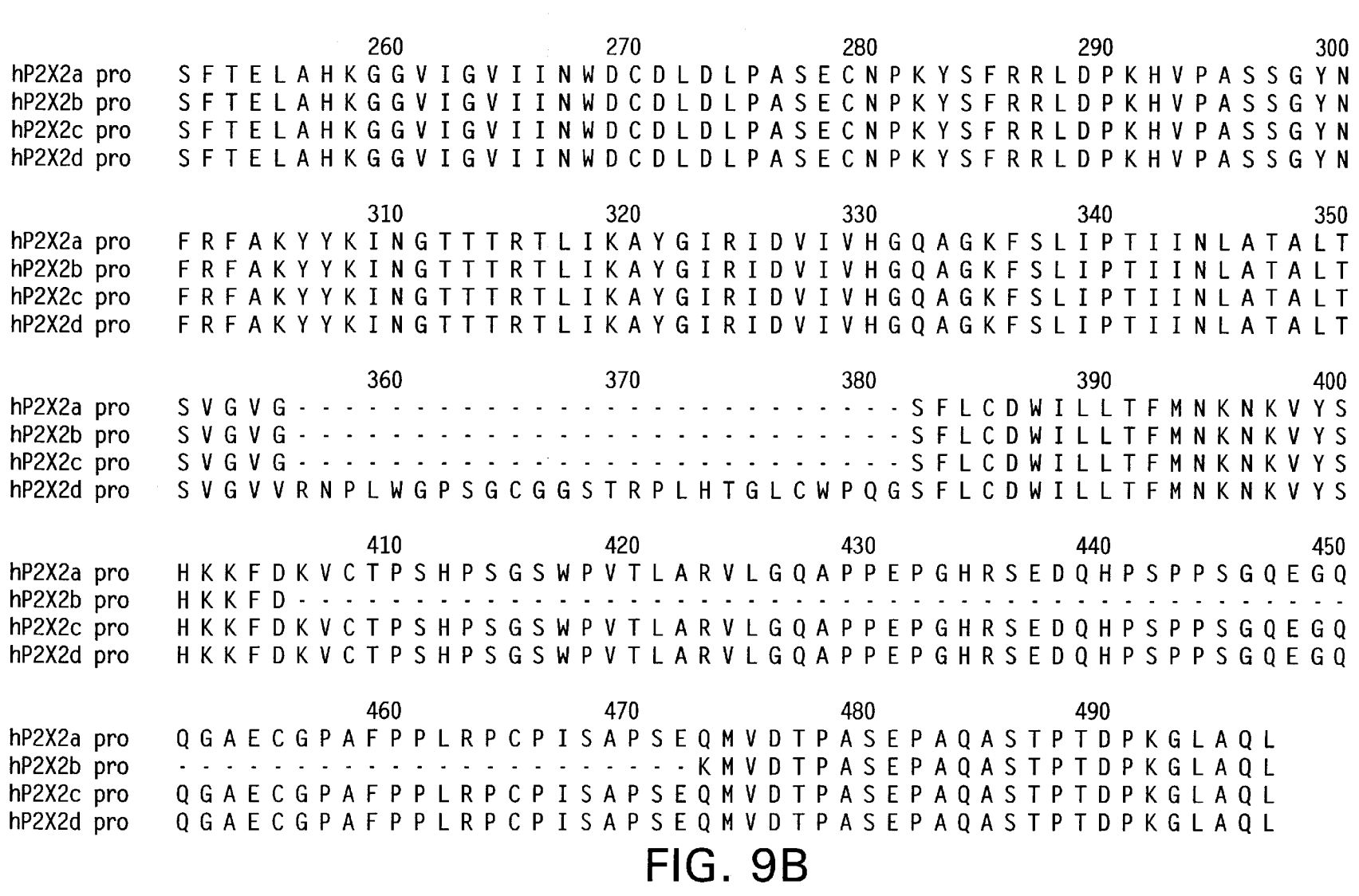

A proofreading thermostable polymerase (Cloned Pfu DNA Polymerase, Stratagene Inc. La Jolla, Calif.) was used in the amplification to ensure high-fidelity amplification. The reaction mixture consisted of: 2 µl cDNA, 5 µl 10×cloned Pfu polymerase reaction buffer (200 mM Tris-HCl (pH 8.8), 100 mMKCl, 100 mM$(NH_4)_2SO_4$, 20 mM $MgSO_4$, 1% Triton X-100, 1 mg/ml nuclease-free bovine serum albumin), 1 µl dNTP mix, 1 µl (10 picomoles) 5'$hP2X_2$ primer, 1 µl (10 picomoles) 3'$hP2X_2$ primer, and 39 µl $dH_2O$. The reaction was heated to 95° C. for 1 min., then held at 80° C. for 2 min., during which 1 µl (2.5 units) cloned Pfu polymerase was added. The reaction was cycled 35 times under these conditions; 94° C. for 15 sec., 60° C. for 20 sec., and 72° C. for 5 minutes. After cycling, the reaction was incubated for 10 minutes at 70° C. The reaction products were separated on a 0.8% agarose gel and products of approximately 1.5 kilobases were excised and purified via the Qiaquick gel purification system (Qiagen, Inc., Chatsworth, Calif.). The DNA was eluted with 50 µl $dH_2O$, lyophilized and resuspended in 10 µl $dH_2O$. The DNA was eluted with 50 µl $dH_2O$, lyophilized and resuspended in 15 µl $dH_2O$. Three microliters of the purified PCR product was used in a ligation reaction using the pCRscript cloning system (Stratagene) which also included: 0.5 µl (5 ng) of the pCRscript Amp SK(+) vector, 1 µl of pCRscript 10×Reaction Buffer, 0.5 µl of 10 mM ATP, 1 µl (5 units) Srf 1 restriction enzyme, 1 μl (4 units) T4 DNA ligase, and 3 μl dH$_2$O. The reaction was incubated at room temperature for one hour, then at 65° C. for 10 minutes. One microliter of this reaction was used to transform ultracompetent DH-5-α (Gibco BRL) as per standard manufacturer's protocols. Resulting clones were screened by restriction analysis and sequenced using fluorescent dye-terminator reagents (Prism, Perkin Elmer Applied Biosystems) and an Applied Biosystems 310 DNA sequencer. Three species of cDNAs containing intact open reading frames from the predicted initiation to termination codons were isolated (FIG. 7, hP2X$_{2b}$, c, d). Based on structural similarity to the rat P2X$_2$ receptor, a fourth species, (hP2X$_{2a}$, FIG. 7a) was created by joining nucleotides 1–666 (using adenine of the initiation codon as nucleotide #1) of hP2X$_{2d}$ with nucleotides 595–1349 of hP2X$_{2c}$. The predicted polypeptides encoded by these cDNAs are shown in FIG. 8. An alignment of the predicted amino acid sequences are shown in FIG. 9.

EXAMPLE 3

Expression and Electrophysiological Analysis of Recombinant P2X$_2$ Receptors in Xenopus Oocytes To assess function of the human P2X$_2$ receptors, RNA was synthesized from the clones using the T$_7$ bacterial promoter present on the pCRscript vector and reagents from Ambion (Message Machine; Ambion, Inc., Austin Tex.).

1. Preparation and Injection of Oocytes

Adult female frogs (*Xenopus laevis*) were anesthetized with 0.2% tricaine before surgery. During surgery, sections of one ovary were removed and oocytes were denuded of overlying follicle cells by agitation for 1–2 hours in 2 mg/ml collagenase (Sigma type IA) in low-Ca$^{2+}$ Barth's solution containing (in mM): 88 NaCl, 2.5 KCl, 1.0 MgCl$_2$ 10 Na-HEPES (pH 7.4) plus 100 μg/ml gentamicin. Selection of stage V and VI oocytes was begun after approximately 50% of the cells were denuded. Cytoplasmic injections of 50 ng hP2X$_{2a-d}$ RNA were performed on denuded oocytes using a glass microelectrode. Only one receptor subtype RNA was injected per cell. Oocytes were used for recording 1–2 days after injection and were maintained at 16–19° C. in normal Barth's solution (incubation medium in mM): 90 NaCl, 1.0 KCl, 0.66 NaNO$_3$, 0.74 CaCl$_2$, 0.82 MgCl$_2$, 2.4 NaHCO$_3$, 2.5 Na-pyruvate, 10 Na-HEPES (pH 7.4) plus 100 μg/ml gentamicin.

2. Recording Solutions and Chemicals

The standard recording solution contained (in mM): 96 NaCl, 2.0 KCl, 1.8 BaCl$_2$, 1.0 MgCl$_2$, 5.0 Na-pyruvate, and 5.0 Na-HEPES (pH 7.4). BaCl$_2$ was replaced with CaCl$_2$ (1 mM) in some experiments without significant effects on the pharmacological properties of the receptors. All oocyte solutions were diluted in distilled H$_2$O from 10×stock solutions. Concentrated stocks of agonists and antagonists were made in distilled H$_2$O and then serially diluted in recording solution to desired final concentrations. All chemicals and agonists (ATP and α,βme-ATP) were obtained from Sigma Chemical Company.

3. Electrophysiological Recordings

Transmembrane currents were recorded using two-electrode voltage-clamp techniques with an Axoclamp-2 A amplifier, and were collected and analyzed using pCLAMP software (Axon Instruments). Electrodes (1.5–2.0 M'Ω) were filled with 120 mM KCl. Responses to ATP and α,βme-ATP were routinely recorded at room temperature while the oocyte membrane was voltage-clamped at −60 mV. Agonists were applied using a computer-controlled small diameter drug application pipette positioned close to the oocyte in the perfusion chamber. Application duration typically lasted 5–10 sec. The peak amplitude of the ATP-activated inward current was used for determining EC$_{50}$ values.

4. Results hP2X$_{2a}$ and hP2X$_{2b}$ receptors—Transient external application of ATP to oocytes expressing hP2X$_{2a}$ or hP2X$_{2b}$ receptors produced a concentration-dependent increase in net inward current (FIG. 10, panels A and B). Peak inward current increased with increasing ATP concentrations, consistent with an increase in probability of agonist binding, and therefore receptor activation. Concentration-response curves for four hP2X$_{2a}$ cells revealed a mean ATP EC$_{50}$ of 16 μM, and a Hill coefficient (n$_H$) of 1.5. Concentration-response curves for three hP2X$_{2b}$ cells revealed a mean ATP EC$_{50}$ of 20 μM, and a n$_H$ of 1.5. Both receptor subtypes exhibited reversible non-desensitizing response kinetics. Application of another P2X receptor agonist, αβMethylene-ATP (αβMe-ATP) had no effect on hP2X$_{2a}$ or hP2X$_{2b}$ receptors at a concentration of 100 μM.

5. hP2X$_{2c}$ and hP2X$_{2d}$ Receptors

Transient external application of ATP (30 μM) to oocytes injected with hP2X$_{2d}$ or hP2X$_{2d}$ RNA had no effect (FIG. 10, panels C and D).

6. Conclusions

Using an electrophysiological approach to analyze hP2X$_{2a-d}$ receptor function, we have shown that two receptor subtypes (hP2X$_{2a}$ and hP2X$_{2b}$) can be selectively activated by ATP, but not αβMe-ATP. These responses are also non-desensitizing. The hP2X$_{2c}$ and hP2X$_{2d}$ subtypes expressed alone did not respond to ATP. These data support the formation of functional homomeric recombinant hP2X$_{2a}$ and hP2X$_{2b}$ ion channel receptors.

EXAMPLE 4

Identification of a Human Sequence with Homology to P2X Receptors

The predicted amino acid sequence of the rat P2X$_4$ receptor (Genbank accession #X91200) was used to search for human DNA sequences that would code for similar polypeptides. The TBLASTN database search tool (Altschul (1993) *J. Mol. Evol.* 36:290–300) was used, which allows querying nucleotide databases with a protein sequence by dynamically translating the DNA sequences into all six possible reading frames. A search of the Lifeseq database (Incyte Pharmaceuticals, Inc., Palo Alto, Calif.) revealed a partial sequence of a cDNA clone derived from human knee synovium from a patient with rheumatoid arthritis with a high degree of homology to a region of the rat P2X$_4$ receptor cDNA. The database entry for this sequence (Incyte clone #1260936) is shown below:

GCGGGNCCATGGCGGGCTGCTGCGC-
CGCGCTGGGNGCCCTTTCCTGTTCG AGTACGA-
CACGCCGCGCATCGTGCTCATCCGCAGC-
CGCAAAGTGGGGCT
CATGMCCGCGCCGTGCAACTGCTCATC-
CTGGCCTACGTCATCGGGT (SEQ ID NO:4) (where N=A, T, G, or C) (SEQ ID NO:24)

This cDNA clone was ordered from lncyte, and additional clones from the Incyte database and the Genbank dbEst database were also aligned to the rat P2X$_4$ receptor sequence. Information from these sequences was compiled and used to design primers for PCR amplification of the intact open reading frame (ORF) for the human P2X$_4$ receptor from clone 1260936. (No single sequence among those compiled was sufficient to produce a functional polypeptide.) The sequence immediately upstream of the initiation codon of the ORF was modified in the design of the primers to incorporate a consensus translation initiation signal to optimize gene expression (Kozak (1984) *Nucl. Acids Res.* 12:857–872). The sequence of the two P2X$_4$ primers are:

5'-GCGCCACCATGGCGGGCTGCTGCGCCGCGCTG-3' (sense) (SEQ ID NO:25) and 5'-GGTAGGCCTCACTGGTCCAGCTCACTAGCAAG-3' (antisense) (SEQ ID NO:26).

EXAMPLE 5

Subcloning of the ORF for the Human $P2X_4$ Receptors

To facilitate transfer of the open reading frame of the human $P2X_4$ receptor, polymerase chain amplification reactions were used on the Incyte clone 1260936 using the primers designed from the consensus sequence of the predicted 5' and 3' ends of the open reading frame. Template DNA (100 ng) was used in a 100 µl amplification reaction that also included 200 µM dNTPs, 15 pmoles each primer, 10 µ0 10×GeneAmp PCR buffer (Perkin Elmer, Foster City, Calif.) (500 mM KC1, 100 mM Tris-HCl pH 8.3, 15 mM MgCl2, and 0.01% (w/v) gelatin), and 0.5 µl (2.5 units) Ampliaq® polymerase (Perkin Elmer). The reaction was cycled 35 times in a Perkin Elmer Model 9600 thermocycler under the following conditions: 95° C. for 30 sec, 55° C. for 30 sec, and 72° C. for 2 min. The predominant product of 1.2 kilobase pairs was isolated by electrophoresis on a 1% low melting point agarose gel and purified. A portion of the purified product (10%) was used in a ligation reaction with the vector pCRII (Invitrogen, Carlsbad, Calif.) using the manufacturer's protocols. The ligation products were used to transform competent DH5-alpha *E. coli*. Resulting clones were screened by restriction analysis and a representative clone was sequenced using fluorescent dye-terminator reagents (Prism, Perkin Elmer-Applied Biosystems Division) and a Perkin Elmer-Applied Biosystems Model 373 DNA sequencer. The insert from this clone was excised from the vector using the restriction enzyme EcoRI and was used in a ligation reaction with the mammalian expression vector pCDNA3.1(+) (Strategene, La Jolla, Calif.). Reaction products were used to transform competent *E. coli* and resulting clones were screened by restriction analysis. A representative clone was sequenced. The sequence of the insert is shown in FIG. 11. To guard against sequence errors introduced by the DNA amplification process, the ORF contained in the original Incyte clone 1260936 was also sequenced and found to be identical to that of the expression clone. A comparison of the predicted protein sequence of the human $P2X_4$ to that of the rat receptor is depicted in FIGS. 12A and 12B.

EXAMPLE 6

Electrophysiological Analysis of Recombinant $P2X_4$ Receptors Expressed in Xenopus Oocytes The preparation of *Xenopus laevis* oocytes, injection with receptor RNA or DNA, and measurement of receptor responses using two-electrode voltage-clamp followed procedures described previously (Briggs et al. (1995), supra). Oocytes were maintained at 17–18° C. in normal Barth's solution (90 mM NaCl, 1 mM KCl, 0.66 mM $NaNO_3$, 0.74 mM $CaCl_2$, 0.82 mM $MgCl_2$, 2.4 mM NaHCO°, 2.5 mM sodium pyruvate, and 10 mM Na N-(2-hydroxyethyl)-piperazine-N'-(2-ethanesulfonic acid) ("HEPES") buffer, final pH 7.55) containing 100 µg/ml gentamicin. Responses were measured at a holding potential of –60 mV in modified Barth's solution containing 10 mM $BaCl_2$ and lacking $CaCl_2$ and $MgCl_2$. However, in some experiments, the cell potential was intentionally varied in order to determine the response current-voltage relationship. Agonist was applied briefly using a computer-controlled solenoid valve and a push/pull applicator positioned to within 200–400 µm from the oocyte. Responses were recorded by computer in synchrony with agonist application. Antagonists were included with agonist in the push/pull applicator and were applied to the bath by superfusion for at least 3 minutes before application of agonist. Responses were quantified by measuring the peak amplitude.

DNA for injection into oocytes was the $P2X_4$ insert from pCDNA3.1 prepared as described in Example 2. The clone was grown up and prepared in large scale using the QIAgen maxiprep DNA preparation system according to the manufacturer's instructions. The DNA was ethanol precipitated and resuspended in TE buffer. For RNA production, the $P2X_4$-pCNDA3.1 cvonstruct was linearized by digestion with the restriction enzyme NotI and $P2X_4$ messenger RNA was produced using the T7 promoter in this vector and the Ambion mMessage mMachine in vitro transcription kit according to the manufacturer's instructions.

For functional analysis of human $P2X_4$ receptors, 10 ng of human $P2X_4$ receptor DNA prepared as described above was injected into the nucleus of Xenopus oocytes. Alternatively, 50 ng of human $P2X_4$ receptor RNA prepared as described above was injected into the ooxyte cytoplasm. Oocytes were incubated in normal Barth's solution containing 100 µg/ml gentamicin for 2–7 days following injection. The response to 10 µM ATP was then recorded.

Oocytes injected with human $P2X_4$ receptor DNA responded to extracullular application of ATP by exhibiting a mixed-conductance cation current (100–1000 nA). Oocytes injected with an appropriate amount of water did not respond to ATP. An approximate ATP $EC_{50}$ of 2 µM was obtained from concentration-response relationships (0.1–1000 µM ATP) from these injected oocytes. ATP-induced current-voltage relationships were also recorded from these oocytes. These revealed a reversal potential of approximately zero mV, with a rather linear slope conductance between –60 and +60 mV. Some inward rectification was noted at more negative membrane potentials. The nonspecific P2X receptor antagonist suramin (10 µM) failed to depress ATP (10 µM)-induced currents in these cells.

Oocytes injected with human $P2X_4$ receptor RNA responded to ATP application with responses similar to those recorded from DNA-injected cells. ATP concentration-response curves from these injected oocytes revealed an $EC_{50}$ of 1–2 µM ATP. Another P2X receptor agonist, α,β-methylene-ATP, elicited maximal currents in these oocytes that were only 20–25% of maximal ATP currents. Current-voltage relatiionships also showed weak inward rectification, with relatively linear slope conund the reversal potential of zero mV. Functional antagonism of responses was determined by application of nonspecific P2X receptor antagonists suramin or pyridoxal-phosphate-6-azophenyl-2', 4'-disulfonic acid (PPADS). Suramin (1 µM or 10 µM) failed to depress ATP (3 µM) responses, and 100 µM suramin depresesed the responses to approximately 80% of control. PPADS antagonized ATP responses with an estimated $IC_{50}$ to 30 µM.

In summary, injection of human $P2X_4$ receptor DNA into Xenopus oocytes resulted in expression of functional $P2X_4$ receptors on the cell surface, and these receptors function as ligand-gated nonspecific cation channels. These receptors respond to extracellular ATP ($EC_{50}$=1–2 µM), exhibit moderate inward rectification, and are blocked by PPADS, but are relatively insensitive to suramin.

3'RACE products, including a poly A stretch of variable length, is shown in FIG. 4 (SEQ ID NO:8). With the exception of variable lengths of polyadenlyation, this region was also found to be identical in each of the two sized clones.

What is claimed is:

1. An isolated polynucleotide encoding a polypeptide comprising an amino acid sequence selected from the group consisting of SEQ ID NO:17, SEQ ID NO:18, SEQ ID NO:19 and SEQ ID NO:20.

2. A polynucleotide according to claim 1, wherein the polynucleotide is a polydeoxyribonucleotide (DNA).

3. A polynucleotide according to claim 1, wherein the polynucleotide is a polyribonucleotide (RNA).

4. An expression vector comprising a polynucleotide according to claim 1 operably linked to control sequences that direct the transcription of the polynucleotide, whereby the polynucleotide is expressed in a host cell.

5. A host cell comprising an expression vector according to claim 4.

6. A host cell according to claim 5, wherein the cell is selected from the group consisting of a bacterial cell, a mammalian cell, a yeast cell and an amphibian cell.

7. A host cell according to claim 6, wherein the cell is an amphibian cell.

8. A host cell according to claim 6, wherein the cell is a mammalian cell.

9. An isolated DNA polynucleotide, wherein the DNA comprises a nucleic acid sequence selected from the group consisting of SEQ ID NO:2, SEQ ID NO:13, SEQ ID NO:14, SEQ ID NO:15, and SEQ ID NO:16.

10. A host cell comprising a polynucleotide according to claim 1 or claim 9.

11. A host cell according to claim 10, wherein said cell is selected from the group consisting of a bacterial cell, a mammalian cell, a yeast cell and an amphibian cell.

12. A host cell according to claim 11, wherein the cell is an amphibian cell.

13. A host cell according to claim 11, wherein the cell is a mammalian cell.

14. An expression vector comprising a polynucleotide which encodes a human polypeptide, wherein the polypeptide comprises an amino acid sequence selected from the group consisting of SEQ ID NO:17, SEQ ID NO:18, SEQ ID NO:19, and SEQ ID NO:20.

15. A host cell comprising the expression vector of claim 14.

16. A host cell according to claim 15, wherein the cell is selected from the group consisting of a bacterial cell, a mammalian cell, a yeast cell and an amphibian cell.

17. A host cell according to claim 16, wherein the cell is an amphibian cell.

18. A host cell according to claim 16, wherein the cell is a mammalian cell.

19. A method for producing a human $P2X_2$ receptor polypeptide, the method comprising the steps of:
   (a) culturing a host cell containing an expression vector under conditions that allow the production of the polypeptide, wherein said expression vector comprises a polynucleotide, comprising a nucleic acid sequence selected from the group consisting of SEQ ID NO:2, SEQ ID NO:13, SEQ ID NO:14, SEQ ID NO:15 and SEQ ID NO:16, encoding a human P2X2 receptor polypeptide, said polynucleotide being operably linked to control sequences that direct the transcription of the polynucleotide; and
   (b) recovering the polypeptide.

20. A method for producing a human $P2X_2$ receptor polypeptide, the method comprising the steps of:
   (a) culturing a host cell containing an expression vector under conditions that allow the production of the polypeptide, wherein said expression vector comprises a polynucleotide operably linked to control sequences that direct the transcription of the polynucleotide, wherein said polynucleotide encodes for a human $P2X_2$ receptor polypeptide selected from the group consisting of SEQ ID NO:17, SEQ ID NO:18, SEQ ID NO:19 and SEQ ID NO:20; and
   (b) recovering the polypeptide.

* * * * *